US012779172B2

(12) United States Patent
Hang et al.

(10) Patent No.: US 12,779,172 B2
(45) Date of Patent: Nov. 3, 2026

(54) IMAGE GUIDED CATHETER INSERTION SYSTEM AND METHOD

(71) Applicant: B. Braun Melsungen AG, Melsungen (DE)

(72) Inventors: Jo Ann Hang, Penang (MY); Jien Wei Chai, Penang (MY)

(73) Assignee: B. Braun Melsungen AG (DE)

( * ) Notice: Subject to any disclaimer, the term of this patent is extended or adjusted under 35 U.S.C. 154(b) by 0 days.

(21) Appl. No.: 18/039,801

(22) PCT Filed: Dec. 3, 2021

(86) PCT No.: PCT/EP2021/084227
§ 371 (c)(1),
(2) Date: Jun. 1, 2023

(87) PCT Pub. No.: WO2022/117849
PCT Pub. Date: Jun. 9, 2022

(65) Prior Publication Data
US 2024/0017039 A1 Jan. 18, 2024

Related U.S. Application Data

(60) Provisional application No. 63/120,909, filed on Dec. 3, 2020.

(51) Int. Cl.
*A61M 5/42* (2006.01)
*A61M 25/01* (2006.01)
(Continued)

(52) U.S. Cl.
CPC ........ *A61M 25/0105* (2013.01); *A61M 5/427* (2013.01); *G06K 7/1413* (2013.01);
(Continued)

(58) Field of Classification Search
CPC .............. A61M 25/0105; A61M 5/427; A61M 2025/0166; A61M 2205/3306;
(Continued)

(56) References Cited

U.S. PATENT DOCUMENTS

| | | | | |
|---|---|---|---|---|
| 11,413,015 | B2 | 8/2022 | Bard | |
| 2011/0125028 | A1* | 5/2011 | Wood | A61B 5/489 600/476 |

(Continued)

FOREIGN PATENT DOCUMENTS

| | | | | |
|---|---|---|---|---|
| CN | 107041729 A | * | 8/2017 | A61B 5/7203 |
| CN | 108324246 A | | 7/2018 | |

(Continued)

OTHER PUBLICATIONS

International Search Report and Written Opinion for International Application No. PCT/EP2021/084227, dated Feb. 25, 2022, 13 pages.

(Continued)

*Primary Examiner* — Jamie J Atala
*Assistant Examiner* — Mahmoud Kamal Abouzahra
(74) *Attorney, Agent, or Firm* — Buchanan Ingersoll & Rooney PC

(57) ABSTRACT

A vein detection device including a light source operating at a wavelength for penetrating skin of a patient, a stereo camera operating at the wavelength, a communication interface configured to connect to a mobile device, and a processor. The processor configured to control the light source to illuminate a region of the skin, control the stereo camera to capture an image in the illuminated region, process the captured image to detect a vein of the patient illuminated by the light source, reconstruct a three dimensional image of the
(Continued)

100

120 detected vein, and transmit the three dimensional image of the detected vein to the mobile device via the communication interface.

34 Claims, 21 Drawing Sheets

(51) Int. Cl.

| | |
|---|---|
| ***G06K 7/14*** | (2006.01) |
| ***G06V 10/25*** | (2022.01) |
| ***G06V 20/50*** | (2022.01) |
| ***H04N 13/194*** | (2018.01) |
| ***H04N 23/50*** | (2023.01) |
| ***H04N 23/60*** | (2023.01) |
| *H04N 13/254* | (2018.01) |

(52) U.S. Cl.

CPC .............. *G06V 10/25* (2022.01); *G06V 20/50* (2022.01); *H04N 13/194* (2018.05); *H04N 23/555* (2023.01); *H04N 23/64* (2023.01); *A61M 2025/0166* (2013.01); *A61M 2205/3306* (2013.01); *G06V 2201/031* (2022.01); *H04N 13/254* (2018.05)

(58) Field of Classification Search

CPC ...... G06K 7/1413; G06V 10/25; G06V 20/50; G06V 2201/031; H04N 13/194; H04N 23/555; H04N 23/64; H04N 13/254; G06T 2200/24; G06T 2207/20036; G06T 7/593; G06T 2207/10012; G06T 2207/10024; G06T 2207/10048; G06T 2207/30101; A61B 5/0013; A61B 5/6831; A61B 5/7485; A61B 2576/00; A61B 5/489; A61B 5/6898; A61B 5/0059

USPC ............................................................ 348/45

See application file for complete search history.

(56) References Cited

U.S. PATENT DOCUMENTS

| | | | | |
|---|---|---|---|---|
| 2012/0190981 | A1* | 7/2012 | Harris | A61B 5/150954 604/95.01 |
| 2014/0024952 | A1* | 1/2014 | Wood | A61B 5/1172 600/479 |
| 2014/0236019 | A1* | 8/2014 | Rahum | A61B 5/0075 600/473 |
| 2017/0193160 | A1* | 7/2017 | Long | G16H 30/20 |
| 2018/0140784 | A1* | 5/2018 | Haverman | A61M 5/427 |
| 2020/0202517 | A1* | 6/2020 | Venkatesan | A61B 90/36 |
| 2020/0230391 | A1 | 7/2020 | Burkholz et al. | |
| 2020/0323427 | A1 | 10/2020 | Gharib et al. | |
| 2022/0401157 | A1 | 12/2022 | Sowards et al. | |
| 2023/0011437 | A1 | 1/2023 | Sowards et al. | |

FOREIGN PATENT DOCUMENTS

| | | | | |
|---|---|---|---|---|
| CN | 110223280 | A | 9/2019 | |
| CN | 111096796 | A * | 5/2020 | A61B 5/4824 |
| CN | 111553322 | A | 8/2020 | |
| EP | 2654593 | A1 | 10/2013 | |
| WO | 2010029521 | A2 | 3/2010 | |

OTHER PUBLICATIONS

International Preliminary Report on Patentability and Written Opinion for International Application No. PCT/EP2021/084227, issued May 30, 2023, 11 pages.

Office Action (Communication pursuant to Article 94(3) (EPC) issued Aug. 19, 2025, by the European Patent Office in corresponding European Patent Application No. 21 823 297.3-1113. (7 pages).

Office Action (First Office Action) with Search Report issued Jul. 7, 2025, by the National Intellectual Property Administration, P. R. China in corresponding Chinese Patent Application No. 202180081436.6. (21 pages).

Office Action (The Second Office Action) issued Apr. 23, 2026, by the National Intellectual Property Administration, P. R. China in corresponding Chinese Patent Application No. 202180081436.6 and an English translation of the Office Action. (18 pages).

* cited by examiner

100

120

130

200

300

400

402

404

620

640

700

820

940

IMAGE GUIDED CATHETER INSERTION SYSTEM AND METHOD

CROSS REFERENCE TO RELATED APPLICATION

This application is a U.S. National Phase application of PCT International Application No. PCT/EP2021/084227, filed Dec. 3, 2021, which claims benefit of priority from U.S. Provisional Application No. 63/120,909, filed Dec. 3, 2020, both of which are incorporated herein by reference in their entireties.

FIELD OF INVENTION OF THE INVENTION

The subject matter disclosed herein relates to devices, systems and methods for providing image guided catheter insertion.

BACKGROUND OF THE INVENTION

Every year, approximately 80% of hospitalized patients require intravenous (IV) therapy. Peripheral intravenous catheter (PVIC) insertion is most commonly performed. Unfortunately, around 26% of patients fail on first-insertion attempts. For pediatric patients, this fail rate is even greater at 51%. This fail rate is due in part to one or more of lack of a visible vein and/or palpable vein, dark skin and obesity. Furthermore, the choice of an appropriate catheter is not always governed by clear and universal guidelines.

SUMMARY OF THE INVENTION

One embodiment includes a vein detection device comprising a light source operating at a wavelength or penetrating skin of a patient, a stereo camera operating at the wavelength, a communication interface configured to connect to a mobile device, and a processor. The processor is configured to control the light source to illuminate a region of the skin, control the stereo camera to capture an image in the illuminated region, process the captured image to detect a vein of the patient illuminated by the light source, reconstruct a three-dimensional image of the detected vein, and transmit the three-dimensional image of the detected vein to the mobile device via the communication interface.

The vein detection device can further comprise an interchangeable adaptor for insertion into a port of a mobile device.

The processor can be further configured to retrieve, via the communication interface, patient information from a (medical) server, and reconstruct the three dimensional image of the detected vein based on the patient information.

The processor can be further configured to instruct the server, via the communication interface, to store the reconstructed three dimensional image of the detected vein.

The processor can be further configured to select an insertion point for a catheter and dimensions of the catheter based on physical characteristics of the detected vein in the three dimensional image, and transmit the selected insertion point to a mobile device.

The operating wavelength of the light source and the stereo camera can be in the near infrared (NIR) spectrum. The vein detection device described herein can include one or more light sources producing light in the wavelength range of 600 nm-800 nm for illuminating the destination vein.

The processor can be further configured to instruct a user of the vein detection device to adjust an orientation of the vein detection device while capturing the image.

The processor can be further configured to reconstruct a three dimensional image of the detected vein by determining a region of interest (ROI), extracting relevant vein features from the ROI and performing 3D point cloud reconstruction of the relevant vein features.

The vein detection device can capture images of the destination vein under illumination using a stereo vision camera system (e.g. two cameras side-by-side) in order to determine depth of the vein.

The stereo vision camera system can include a left camera and a right camera positioned in a side-by-side configuration and separated from each other by a known baseline distance. The left camera and right camera can simultaneously capture two dimensional (2D) images of objects that may represent two points on the destination vein. The pixels of these 2D images can be then processed using stereoscopy techniques to determine three dimensional (3D) coordinates of the destination vein and a resultant 3D reconstructed vein image. From this information, system can determine a depth at which the destination vein lies beneath the skin surface.

The vein detection device can a portable device that illuminates the patient's skin with light that propagates through the various skin layers and anatomical skin features in order to illuminate, locate, and characterize a destination vein. Stereoscopic images can be then captured to generate a 3D reconstruction of the destination vein for display to the care giver.

The vein detection device can include main body which can be made primarily of plastic and optional data port which can be mini universal serial data bus (USB) for insertion into a port of a mobile device. The vein detection device can further include one or more light sources located on main body and one or more stereo cameras including optional optical lenses for focusing. The lens can provide autofocusing on the target vein. In use, the side of vein detection device can be placed at a distance from the skin of the patient. This distance can be based on the focusing capabilities of the camera and any optical lenses used by detection device. This distance can be generally set greater than the minimum focusing distance of the camera/lens configuration in order to capture a sharp and clear image. In one example, this distance may be greater than or equal to four times the focal length of the lens used. For a typical mobile device camera, this may be a few inches. In general, during operation, one or more light sources can be activated to illuminate the skin, and one or more stereo cameras can capture focused images of the illuminated skin layers and vein pattern.

The main body can also include various electronic components. For instance, one or more light sources (e.g. 750 nm LEDs) and one or more stereo cameras can be mounted to printed circuit board which includes, among other features, electronic components such as a processor, memory and communication circuitry. The electronic components inside main body can be connected to data port via wires. In addition to the electronic components, main body may also include optical devices. These optical devices may include one or more of a band pass filter placed in front of stereo cameras to eliminate ambient light, polarizers placed orthogonally over stereo cameras and LEDs to reduce specular reflection from the skin layers, as well as holographic diffusers placed over LEDs to increase optical isotropy.

In one example, the main body of the vein detection device houses near infrared (NIR) light source(s) (e.g. NIR LEDs), stereo cameras (e.g. two CCD sensors), processor with memory, external camera management library, NIR image processing software, catheter selection/insertion software, optional USB interface (or other equivalent wired data interface) and/or optional wireless (e.g. Bluetooth) interface.

During operation, the vein detection device can be either plugged into mobile device via optional data port, or connected wirelessly (e.g. Bluetooth Connection) to mobile device via wireless interface. Once connected, the caregiver can execute a vein detection application installed on mobile device. This application can allow the caregiver to control vein detection device via mobile device (e.g. send/receive data to/from vein detection device), communicate with server (e.g. send/receive data to/from server), and/or enter pertinent information (e.g. patient information, medical procedure information, etc.).

In one example, the caregiver (e.g. phlebotomist) connects (e.g. wired or wireless) mobile device to vein detection device and opens the vein detection application. The caregiver can then enter (e.g. by way of manual entries, barcode scan, quick response (QR) code scan, etc.) patient information (e.g. patient ID) and other information (e.g. prescription) into mobile device. The mobile device can then instruct the caregiver to place vein detection device at a distance from the target area (e.g. arm) of the patient. This distance is based on the focusing capabilities of the camera and any optical lenses used by detection device. This distance can be generally set greater than the minimum focusing distance of the camera lens configuration in order to capture a sharp and clear image.

The vein detection device may be held in place (e.g. on the target are of the patient) by the caregiver. Alternatively, the vein detection device may be held in place and stabilized by a holder, or affixed to the target area of the patient.

In one example, the vein detection device is plugged into a mobile device that is stabilized by a clamped gooseneck holder that can include a mobile device holder, a gooseneck (e.g. flexible jointed metal pipe) connected to mobile device holder and a clamp connected to gooseneck. During operation, the mobile device can be held in place (e.g. under tension) by holder and/or clamp. The mobile device can be clamped to a fixed surface (e.g. table, chair, etc.). Once the clamp is clamped to a fixed surface, gooseneck may be adjusted (e.g. bent) by the caregiver such that the vein detection device is placed at a distance from the skin of the patient based on the focusing capabilities of the camera and any optical lenses used by detection device. The rigidity of gooseneck can stabilize and hold vein detection device in place at a set distance from the patient's skin for the vein scanning procedure. This distance can be based on the focusing capabilities of the camera and any optical lenses used by the vein detection device. This distance can be generally set greater than the minimum focusing distance of the camera lens configuration in order to capture a sharp and clear image.

In another example, the vein detection device is plugged into a mobile device that can be stabilized by a block mounted gooseneck holder that can include a holder, gooseneck (e.g. flexible jointed metal pipe) connected to holder and connected to block base (e.g. weighted block) via adjustment ring that sets an angle of gooseneck relative to block base. During operation, the phone is held in place (e.g. under tension) by holder. Once the phone is held in place, gooseneck may be adjusted (e.g. bent) and adjustment ring may be adjusted (e.g. loosened/tightened) such that vein detection device can be positioned at a distance from the skin of the patient based on the focusing capabilities of the camera and any optical lenses used by detection device. The rigidity of gooseneck can stabilize and hold vein detection device in place at a set distance from the patient's skin for the vein scanning procedure. This distance can be based on the focusing capabilities of the camera and any optical lenses used by detection device. This distance can be generally set greater than the minimum focusing distance of the camera lens configuration in order to capture a sharp and clear image.

In yet another example, the vein detection device is affixed by a strap. During operation, the caregiver can position the vein detection device at a distance from the skin of the patient. This distance may be accomplished by use of a spacer positioned in between vein detection device and the user's arm. The caregiver then can affix the vein detection device and spacer to the target area by wrapping strap (e.g. cloth or the like) around the patient (e.g. around the arm) and connecting strap end to strap end (e.g. ends may be Velcro or the like). The strap and spacer can stabilize and hold the vein detection device in place at a set distance from the patient's skin for the vein scanning procedure. This distance can be based on the focusing capabilities of the camera and any optical lenses used by detection device. This distance can be generally set greater than the minimum focusing distance of the camera lens configuration in order to capture a sharp and clear image. Thus, the dimensions (e.g. thickness) of spacer may be set according the focusing capabilities of the camera and optical lenses of detection device. The dimensions of spacer may also be adjustable to accommodate the focusing capabilities of detection devices with different cameras and/or lenses.

Once the vein detection device is positioned, mobile device can instruct the processor of the vein detection device to perform vein detection. Specifically, the processor can turn on NIR light source(s) to illuminate the target area of the patient's skin and/or can turn on stereo camera(s), especially with the aid of external camera management library to capture stereo still images or stereo video of the illuminated target area. The processor can also execute NIR image processing algorithm stored in memory which performs image processing on the captured stereo images/video. In general, the NIR image processing algorithm can extract relevant features (e.g. points on the illuminated target vein) in the captured images/video and reconstructs a 3D image of the target vein using triangulation techniques. The processor can also execute catheter selection/insertion software which analyses one or more of the reconstructed 3D vein image to select an appropriate catheter (e.g. appropriate needle size), an appropriate insertion site and an appropriate insertion angle for the needle insertion procedure. The 3D reconstructed image and the catheter information can be then relayed to mobile device via USB interface or wireless interface and displayed on mobile device for the caregiver.

The vein detection device may also be able to mark or aid in the marking of the insertion site on the patient's skin. In one example, the vein detection device may have a marking arrow that allows the caregiver to mark (e.g. using an ink marker) the insertion site on the patient's skin. The caregiver can then remove vein detection device and insert the catheter needle in the marked location. In another example, the vein detection device may include a marking window (e.g. circular opening) that allows the caregiver to insert the catheter while the vein detection device is still positioned at the distance from the target area on the patient's skin. Any such marking window may be located on the perimeter of body or in the central portion of body. In one example, the processor may relay instructions to the mobile device instructing the caregiver in accurately aligning the marking arrow/window with the appropriate insertion site. In another example, caregiver (e.g. based on experience) may manually select and mark the insertion site based on the displayed 3D image.

Optional server may also aid in the vein detection process. For example, the server may send patient information (e.g. patient age, weight, ID, previous injection results, injection site recommendations, etc.) to the mobile device in order to more accurately control vein detection device. Likewise, the mobile device may send analysis and injection results (e.g. injection success/failure, etc.) back to server to update the patient's profile and medical history. Such information may then be used to update the NIR image processing software and/or the catheter selection software.

The vein detection system may include vein detection device connected (e.g. wired or wirelessly) to mobile device and to (medical) server via wireless (e.g. WiFi) hardware such as gateway/router. In addition, the vein detection system may include a patient bracelet that can include a barcode, QR code, RFID chip, etc. that can be scanned by either the mobile device or the vein detection device to identify the patient and retrieve pertinent patient/procedure information from server.

For example, during operation, the caregiver may capture, via a camera on mobile device, or via the stereo camera(s) on vein detection device an image of patient bracelet. The mobile device may analyse the code on bracelet to determine an identification number. The mobile device may then send this identification number to server (e.g. medical server) via wireless network and gateway/router. Server may retrieve pertinent patient information (e.g. patient ID, medical history, etc.), and procedure information (e.g. prescription). This retrieved information is then sent back to mobile device via gateway/router and wireless network. Upon receiving the retrieved information, the mobile device can instruct vein detection device to perform the vein detection and the catheter selection/insertion algorithm based in part on the retrieved information The vein detection device wherein the mobile device is a smartphone. The vein detection device wherein the vein detection device or the mobile device captures an image of a code on a packaging of a catheter device, on a medication label, on a patient's medical charts or on a patient's wrist band, and the mobile device uses the code to retrieve information relating to at least one of the patient, the catheter device, and the medication.

One embodiment includes a vein detection method comprising the steps of illuminating, by a light source, a region of skin of a patient, the light source operating at a wavelength for penetrating the skin of the patient, capturing, by a stereo camera, an image in the illuminated region, the stereo camera operating at the wavelength, processing, by a processor, the captured image to detect a vein of the patient illuminated by the light source, reconstructing, by the processor, a three dimensional image of the detected vein, and transmitting, by the processor, the three dimensional image of the detected vein to the mobile device via a communication interface.

The vein detection method can further comprise the step of: communicating, by the processor to the mobile device, via an interchangeable adaptor inserted into a port of the mobile device.

The vein detection method can further comprise the steps of: identifying the patient; retrieving, by the processor via the communication interface, patient information from a medical server; and reconstructing, by the processor, the three dimensional image of the detected vein based on the patient information.

The vein detection method can further comprise the steps of: instructing, by the processor via the communication interface, the server to store the reconstructed three dimensional image of the detected vein.

The vein detection method can further comprise the steps of: selecting, by the processor, an insertion point for a catheter and dimensions of the catheter based on physical characteristics of the detected vein in the three dimensional image; and transmitting, by the processor via the communication interface, the selected insertion point to the mobile device.

In the vein detection method the operating wavelength of the light source and the stereo camera can be in the near infrared (NIR) spectrum. The vein detection method can further comprise the steps of: instructing, by the processor, a user of the vein detection device to adjust an orientation of the vein detection device while capturing the image.

The vein detection method can further comprise the steps of: reconstructing, by the processor, the three dimensional image of the detected vein by determining a region of interest (ROI), extracting relevant vein features from the ROI, and performing 3D point cloud reconstruction of the relevant vein features.

The vein detection method can be performed by illuminating the target area (e.g. subcutaneous layer in patient's arm) with NIR light, capturing stereo images, and reconstructing a 3D image of the detected vein. In one example, the processor can execute NIR image processing. Specifically, the processor can remove noise from the captured stereo images. This may be performed via low pass mask filtering of the pixels or the like. The processor can then sharpen and/or brighten the captured stereo images. This may be performed via high pass mask filtering of the pixels or the like. The filtered stereo images can be then segmented such that the processor can determine a region of interest (ROI) (e.g. a segment of the image containing the destination vein). Once the ROI is identified, the processor can extract relevant features (e.g. various points along the vein). The processor can then perform a 3D reconstruction of the vein and determines the appropriate type of catheter to use, insertion site, and insertion angle based on the extracted points. The 3D reconstruction of the vein can be performed based on 3D coordinates and triangulation techniques of the extracted points in the stereo images. Once the 3D reconstruction and catheter selection/insertion algorithm is complete, the 3D image and catheter information can be displayed as output on mobile device.

The vein detection method wherein the mobile device is a smartphone. The vein detection method including capturing, by the processor or the mobile device, an image of a code on a packaging of the catheter, on a medication label, on a patient's medical charts or on a patient's wrist band, and retrieving, by the mobile device using the code, information relating to at least one of the patient, the catheter, and the medication.

In another example, the caregiver can initiate the vein detection system through the mobile software application on mobile device which instructs the caregiver to input patient identification information, for example, by scanning a bar/QR code associated with the patient. The mobile device can then connect to medical server to retrieve any available patient medical records such as care plan and treatment order. For example, patients age, weight, treatment order and infusion flowrate may be retrieved. After vein detection device is placed at the target area, the processor can instruct camera to scan the target area for veins. The processor can analyze the captured image and/or perform techniques such as lazy snapping (e.g. image cutout) to separate unwanted background detail from the veins to define a region of interest (ROI). The processor may convert the image from the red, green, blue (RGB) color model to grayscale. The processor can perform image enhancement by using techniques such as adaptive histogram equalization and filtering to remove noise. The processor can perform binarization of the image by using techniques such as adaptive thresholding due to different depths of the vein pattern. The processor can perform morphological operations to remove noise and insignificant small objects from the background of the image. The processor can perform rectification (e.g. projecting the image onto a common image plane) by establishing an epipolar geometrical constraint based on triangulation. The processor can perform stereo matching to establish a disparity map (e.g. stereo image). The processor performs 3D vein reconstruction by converting the pixel-based disparity values into 3D X, Y and Z coordinates for every pixel. The processor can identify the optimal vein from the 3D image based on vein diameter, depth and length. The processor can determine the vein insertion site, and/or generate a potential catheter gauge, size, length and insertion angle with the aid of an algorithm for catheter length and insertion angle. This information can be then displayed to the caregiver on the screen of the mobile device.

The processing of stereo images, 3D reconstruction of the vein, and the catheter selection/insertion algorithm can be performed by the vein detection device. This processing may alternatively be performed by the mobile device, the server, or any combination of the mobile device, server and vein detection device in order to share the computation load. For example, the vein detection device may simply send the captured stereo images to mobile device which then processes the stereo images, performs 3D reconstruction of the vein, and performs the catheter selection/insertion algorithm with or without the aid of server. Such a load sharing configuration would result in reduced size and cost of vein detection device.

The 3D reconstructed image and catheter information can be displayed on mobile device in order to aid the caregiver in performing a successful catheter insertion. More specifically, this information is displayed as part of a vein detection application being executed on mobile device.

In an example, the vein detection device can be connected (e.g. physically plugged in or wirelessly connected) to mobile device and initialized. The initialization may be performed by opening the vein detection application on mobile device. After initialization, the patient can be identified. This may be performed by manually entering the patient information into mobile device or using the camera of mobile device to capture an image of a barcode or QR code associated with the patient (e.g. printed on a piece of paper, printed on a wristband, displayed on the patient's mobile device, etc.). Once the patient is identified, the mobile device can retrieve patient care information from server which may be a medical server operated by a hospital. The server can retrieve patient information (e.g. patient name, patient age, patient weight, medical history, etc.) and procedure information (e.g. prescription with blood withdrawal instructions). The mobile device may then instruct the caregiver on the selected target location (e.g. arm, hand, neck, etc.) for drawing the blood. Upon receiving the selected target location the caregiver places vein detection device on the target location. The vein detection device may be held in place by the caregiver or affixed (e.g. strapped) to the target area. The vein detection device can scan the target area by illuminating the target area with NIR light sources and capturing stereo images of the illuminated target area. The vein detection device can perform image processing to determine a ROI, extract features from the ROI and construct a 3D image of the vein. In addition, the vein detection device can use the extracted features of the vein to select an appropriate catheter (e.g. size), insertion sight and insertion angle. Once the caregiver completes the catheter needle insertion, the caregiver may also input feedback to the mobile device such as success/failure of the insertion. This information (e.g. catheter information, success/failure of insertion, etc.) can be then sent to server to update the patient's medical records. These records may then be used to aid in future catheter insertions for the patient and for other patients.

One embodiment includes a method for identifying or displaying a suggested catheter insertion point or a catheter insertion method, all of the methods comprising the steps of illuminating, by a light source, a region of skin of a patient, the light source operating at a wavelength for penetrating the skin of the patient, capturing, by a stereo camera, an image in the illuminated region, the stereo camera operating at the wavelength, processing, by a processor, the captured image to detect a vein of the patient illuminated by the light source, reconstructing, by the processor, a three dimensional image of the detected vein, displaying the three dimensional image of the detected vein to the mobile device via a communication interface, and displaying a suggested catheter insertion point on the three dimensional image for guiding a user in the insertion of a catheter.

The method for identifying or displaying a suggested catheter insertion point or the catheter insertion method can further comprise the step of: displaying suggested catheter dimensions for guiding a user in the selection of the catheter.

The method for identifying or displaying a suggested catheter insertion point or the catheter insertion method can further comprise the step of: displaying a suggested catheter insertion angle for guiding a user in the in the insertion of the catheter.

The method for identifying or displaying a suggested catheter insertion point or the catheter insertion method can further comprise the step of: instructing the user to adjust an orientation of the vein detection device while capturing the image.

The method for identifying or displaying a suggested catheter insertion point or the catheter insertion method can further comprise the step of: determining the suggested catheter insertion point based on medical records of the patient.

The method for identifying or displaying a suggested catheter insertion point or the catheter insertion method can further comprise the step of: recording the suggested catheter insertion point in medical records of the patient.

The method for identifying or displaying a suggested catheter insertion point or the catheter insertion method can further comprise the step of: reconstructing, by the processor, the three dimensional image of the detected vein by determining a region of interest (ROI), extracting relevant vein features from the ROI and performing 3D point cloud reconstruction of the relevant vein features.

The method for identifying or displaying a suggested catheter insertion point or the catheter insertion method can further comprise the step of: scanning an image of a barcode or QR code associated with the patient to identify the patient.

The method for identifying or displaying a suggested catheter insertion point or the catheter insertion method can further comprise the step of: retrieving patient care information for the patient.

The method for displaying a suggested catheter insertion point wherein the mobile device is a smartphone. The method for displaying a suggested catheter insertion point including capturing, by the processor or the mobile device, an image of a code on a packaging of the catheter, on a medication label, on a patient's medical charts or on a patient's wrist band, and retrieving, by the mobile device using the code, information relating to at least one of the patient, the catheter, and the medication.

DETAILED DESCRIPTION OF THE INVENTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

INTRODUCTION

The device, system and method described herein provide for the accurate location and characterization of veins in the subcutaneous layer of a patient. The device, system and method described herein also provide instructions for catheter selection and insertions. This provides caregivers (e.g. doctors, nurses, phlebotomists, etc.) with a mechanism for reducing failed catheter insertion attempts. The device, system and method described herein utilize a portable device that illuminates the patient's skin with light that propagates through the various skin layers and anatomical skin features in order to illuminate and detect a destination vein for catheter insertion. The portable device also extracts certain characteristics of the destination vein, including size, to suggest a suitable catheter gauge and length.

Figure 1A:
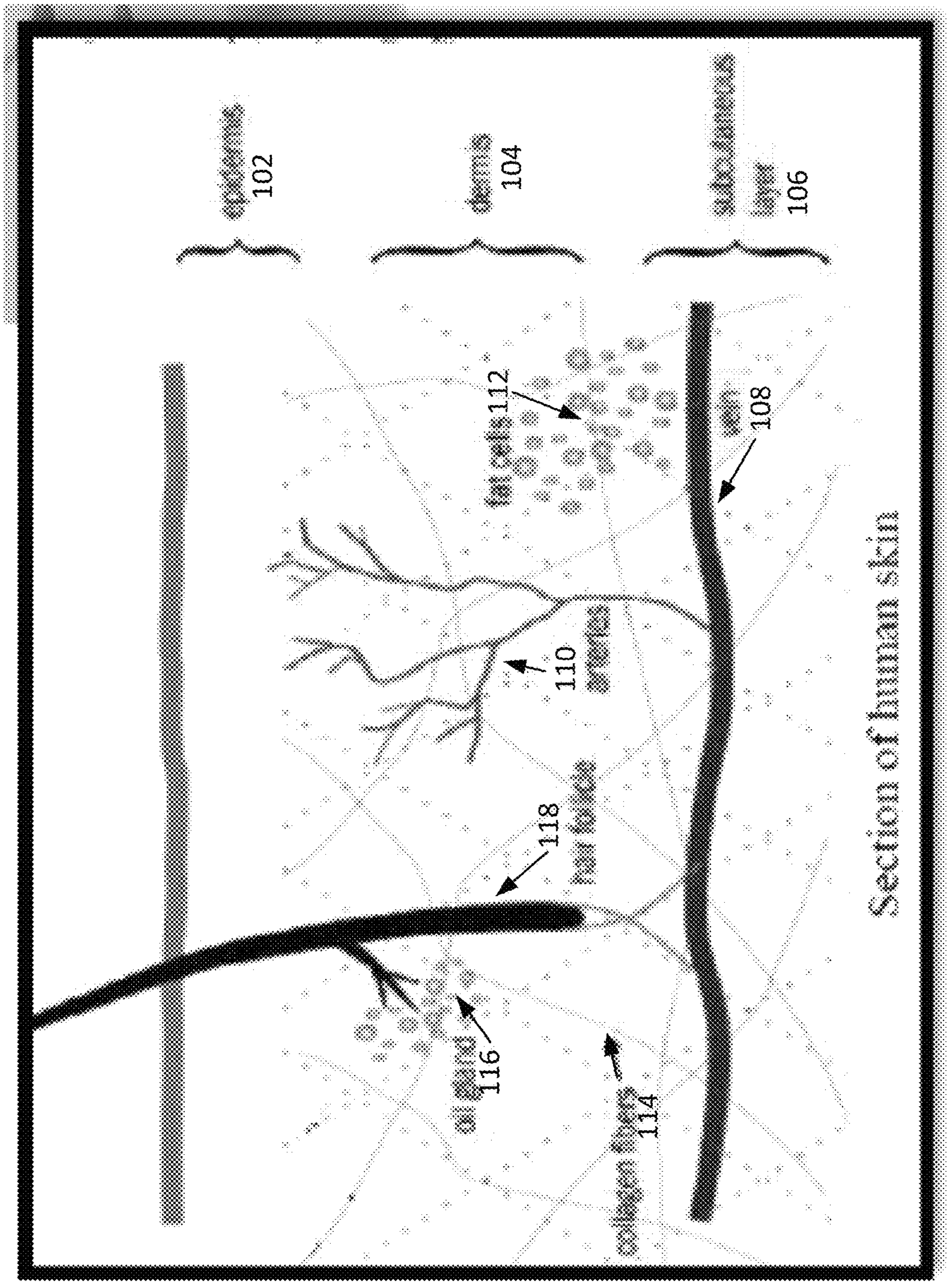
FIG. 1A is a cross-sectional view of a section of human skin, according to an aspect of the disclosure.

FIG. 1A is a cross-sectional view 100 of a section of human skin including epidermis layer 102, dermis layer 104 and subcutaneous layer 106. When inserting an intravenous (IV) catheter needle into the human skin, the needle pierces epidermis 102, passes anatomical skin features of the skin layers, such as arteries 110, fat cells 112, collagen fibers 114, oil glands 116 and hair follicles 118 on its way to reaching and piercing a destination vein 108.

Figure 1B:
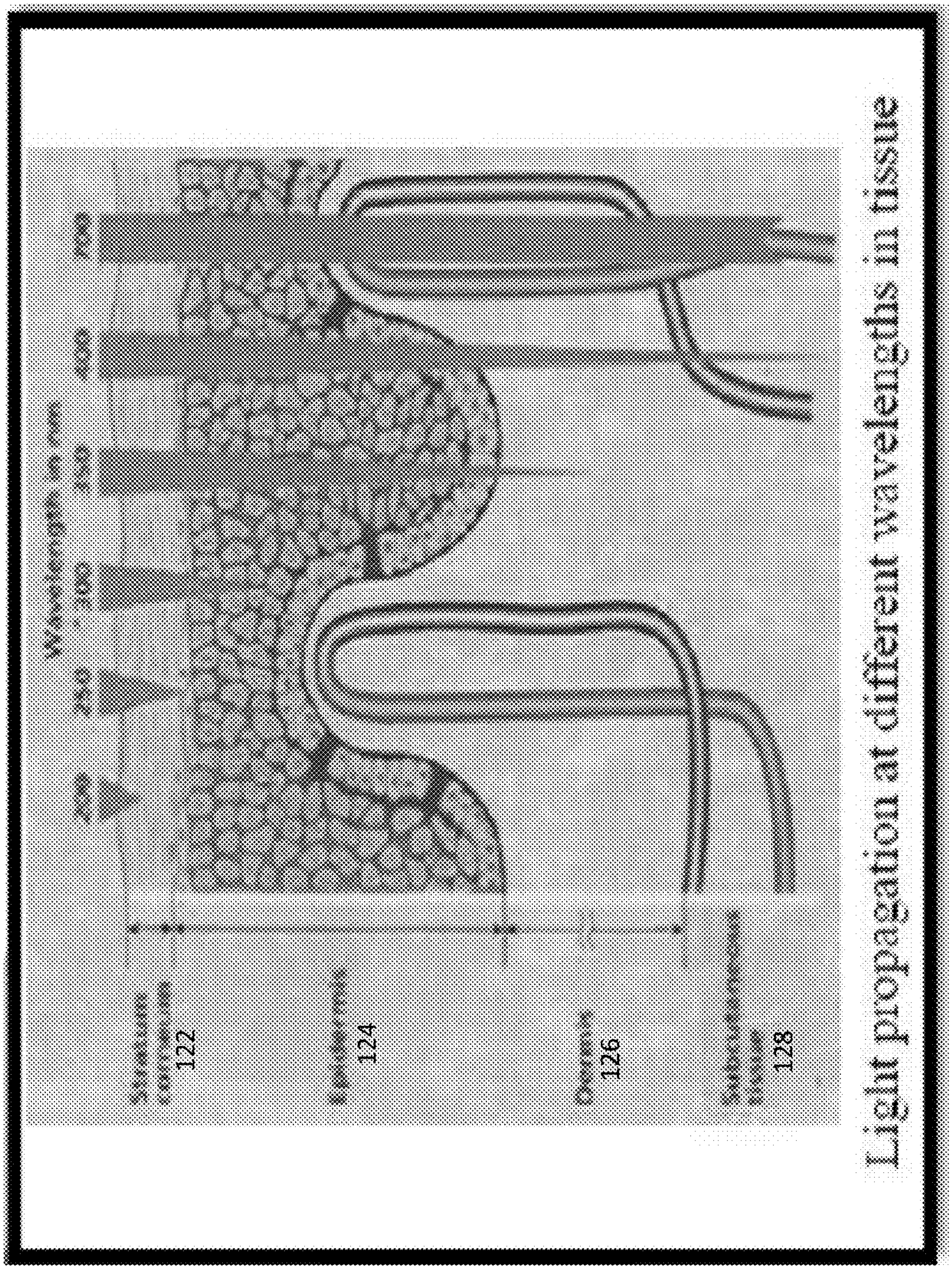
FIG. 1B is a cross-sectional view of light propagation through a section of human skin, according to an aspect of the disclosure.
Figure 1C:
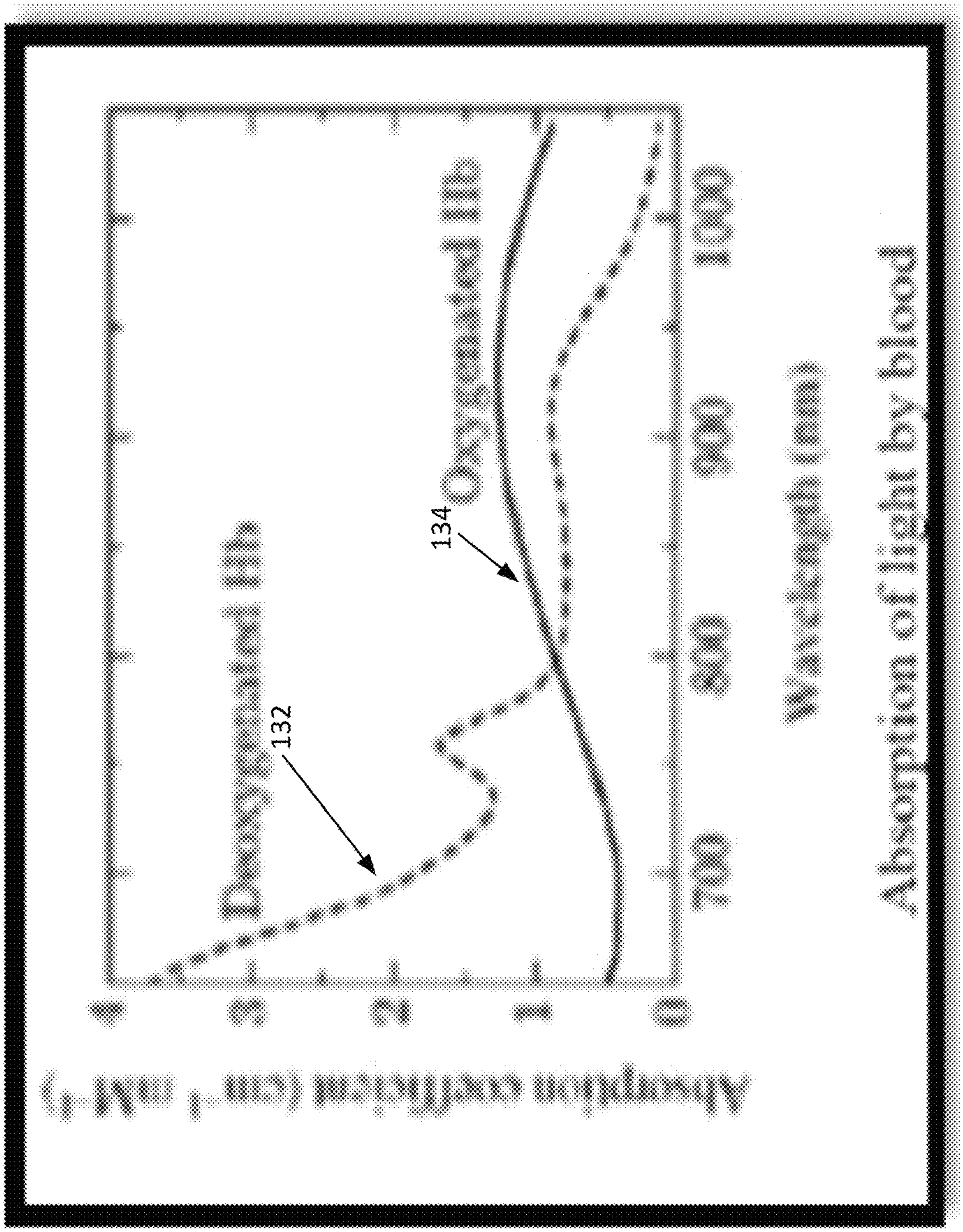
FIG. 1C is a data plot of the absorption of light by blood, according to an aspect of the disclosure.

Illuminating human skin to locate destination vein 108 may be beneficial. However, human skin absorbs light differently depending on the wavelength. For example, FIG. 1B is a perspective view 120 of light propagation through a section of human skin at various wavelengths (e.g. 200 nm-750 nm). As can be seen in FIG. 1B, shorter wavelength light is absorbed in the upper layers of the skin before ever reaching subcutaneous layer 128. A longer wavelength of 600 nm or greater is needed to propagate through the stratum corneum layer 122, epidermis layer 124 and dermis layer 126 in order to reach subcutaneous layer 128 where the destination veins are located. This is further illustrated in FIG. 1C which shows a data plot 130 of the absorption coefficient of light versus wavelength for both deoxygenated hemoglobin (Hb) 132 and oxygenated Hb 134 which is present in the skin layers. Although not necessary, the vein detection device described herein includes one or more light sources producing light in the wavelength range of 600 nm-800 nm for illuminating the destination vein.

In addition to illuminating the destination vein, depth information is important. This lets the caregiver know how deep and at what angle the needled should be inserted. The vein detection device captures images of the destination vein under illumination using a stereo vision camera system (two cameras side-by-side) in order to determine depth of the vein.

Figure 2:
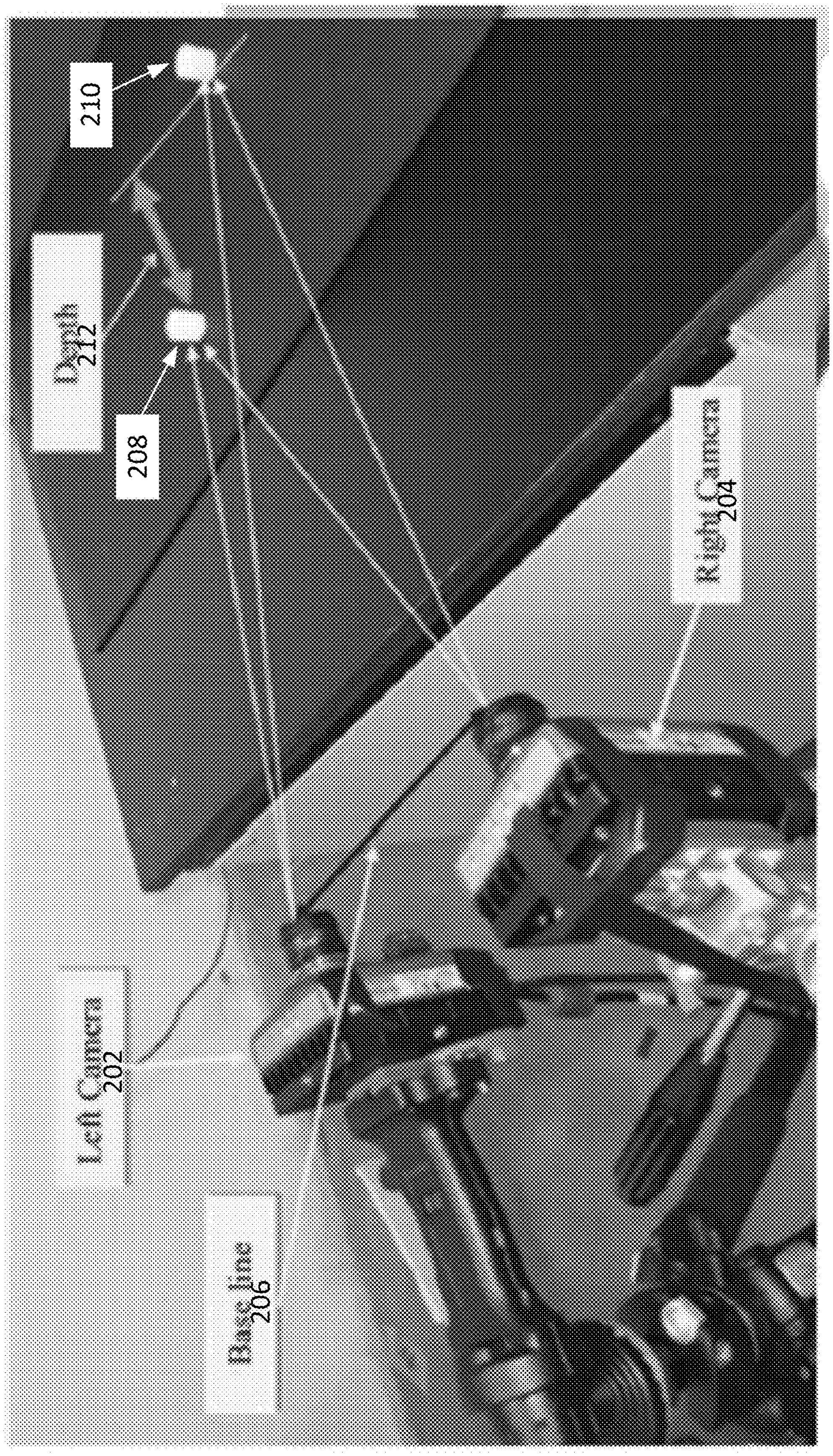
FIG. 2 is a perspective view of a stereo vision camera system, according to an aspect of the disclosure.

One example of a stereo vision camera system 200 according to the present disclosure is shown in FIG. 2. System 200 includes left camera 202 and right camera 204 positioned in a side-by-side configuration and separated from each other by a known baseline distance 206. In general, left camera 202 and right camera 204 simultaneously capture two dimensional (2D) images of objects 208 and 210 that may represent two points on the destination vein. The pixels of these 2D images are then processed using stereoscopy techniques to determine three dimensional (3D) coordinates of the destination vein and a resultant 3D reconstructed vein image. From this information, system 200 can determine a depth 212 at which the destination vein lies beneath the skin surface.

Figure 3:
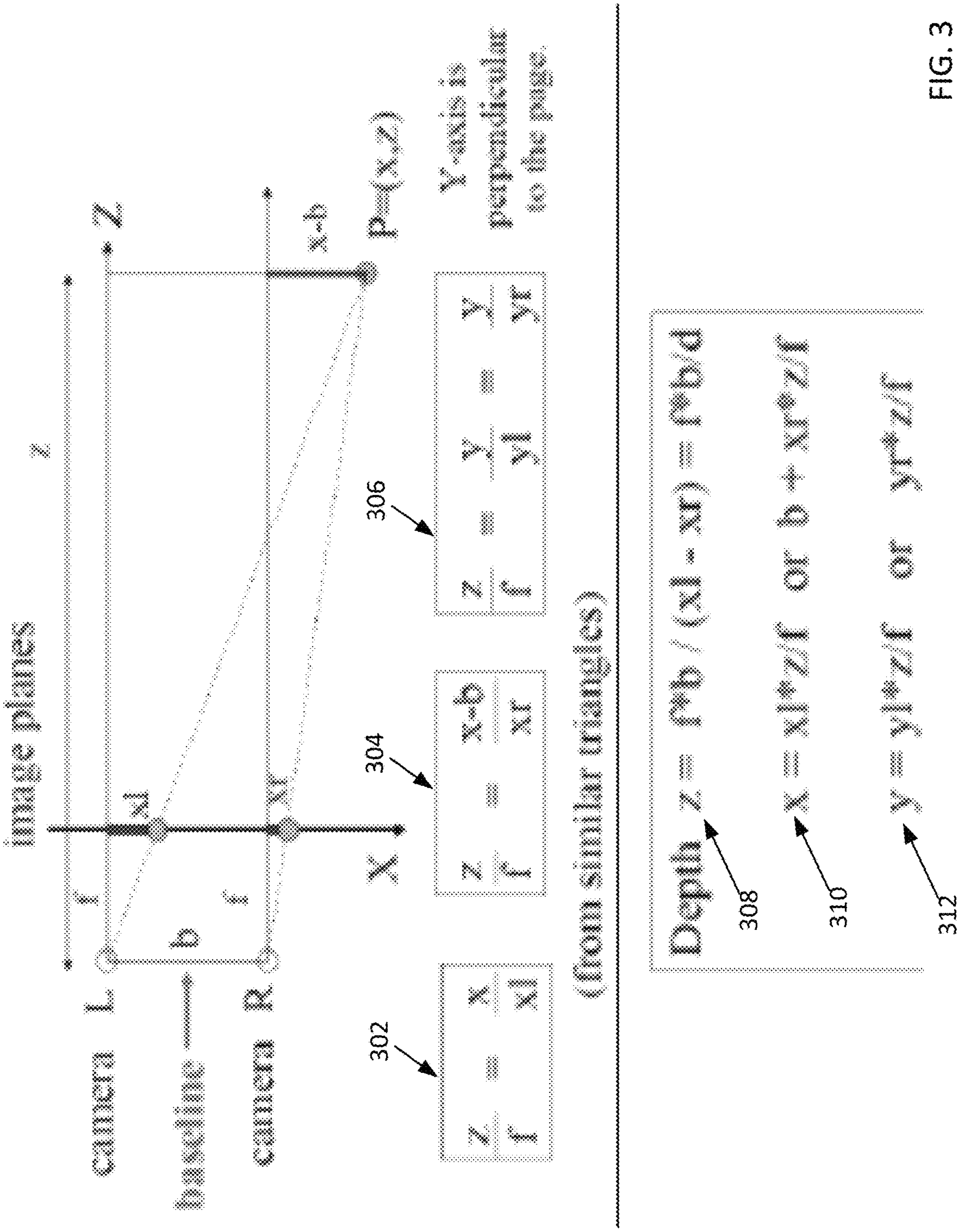
FIG. 3 is a schematic view of projection calculations for a stereo vision camera system, according to an aspect of the disclosure.

Various stereoscopy techniques may be used to generate the 3D reconstructed vein image from the 2D vein images. One such example is shown in schematic 300 of FIG. 3. In this example, point of interest P (e.g. a point on the destination vein) is assigned 3D coordinates x (side to side), y (vertical) and z (e.g. depth 212) based on triangulation methods (see equations 302-312) as measured from the positioning of left camera 202 and right camera 204. In one example, the 3D coordinates of point P (and various other 3D coordinate points) along the length of the destination vein are then reconstructed as a 3D image and displayed on the vein detection device.

Device/System Hardware

As described above, the vein detection device is a portable device that illuminates the patient's skin with light that propagates through the various skin layers and anatomical skin features in order to illuminate, locate, and characterize a destination vein. Stereoscopic images are then captured to generate a 3D reconstruction of the destination vein for display to the care giver.

Figure 4A:
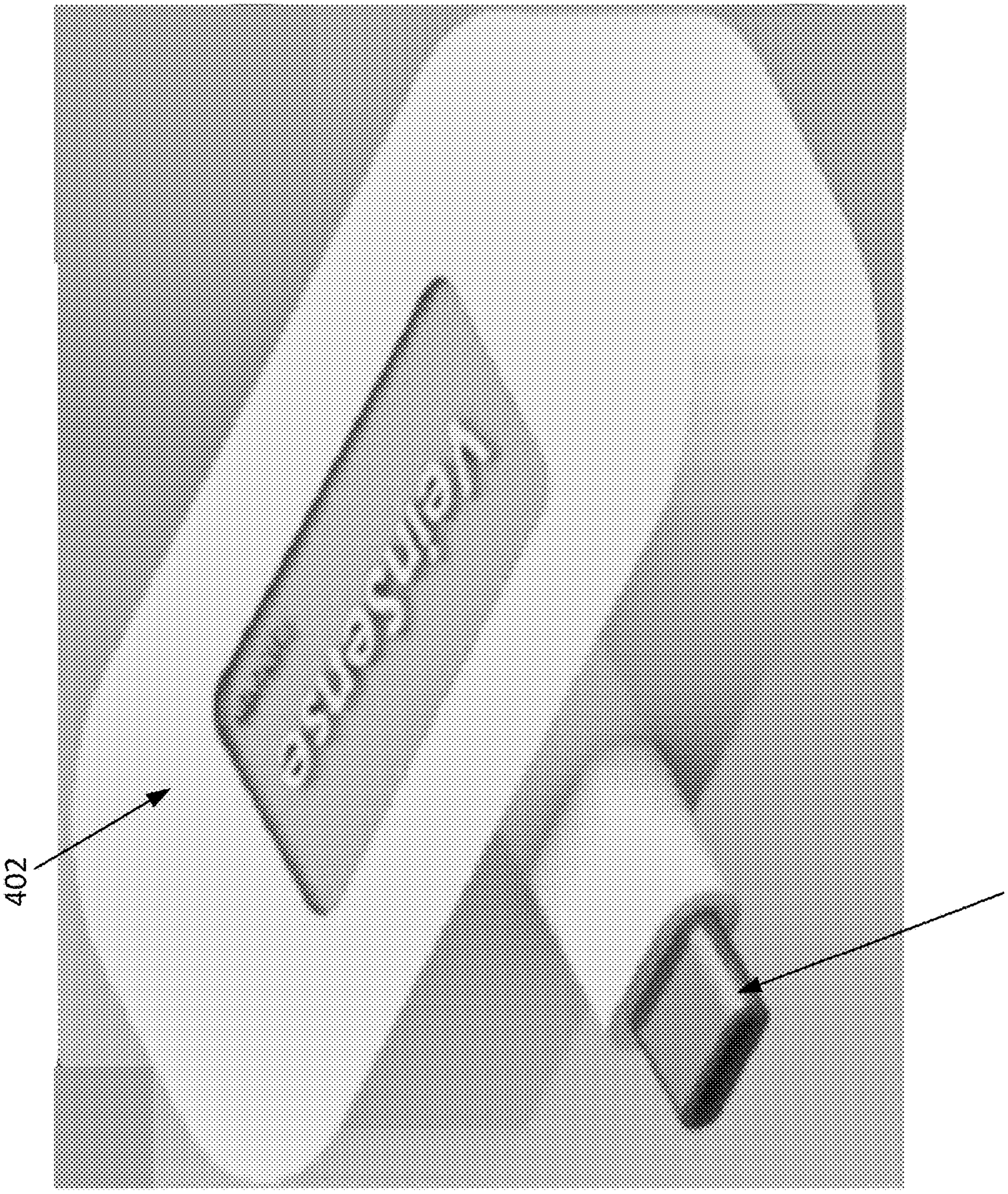
FIG. 4A is a perspective view of a first side of a vein detection device, according to an aspect of the disclosure.
Figure 4B:
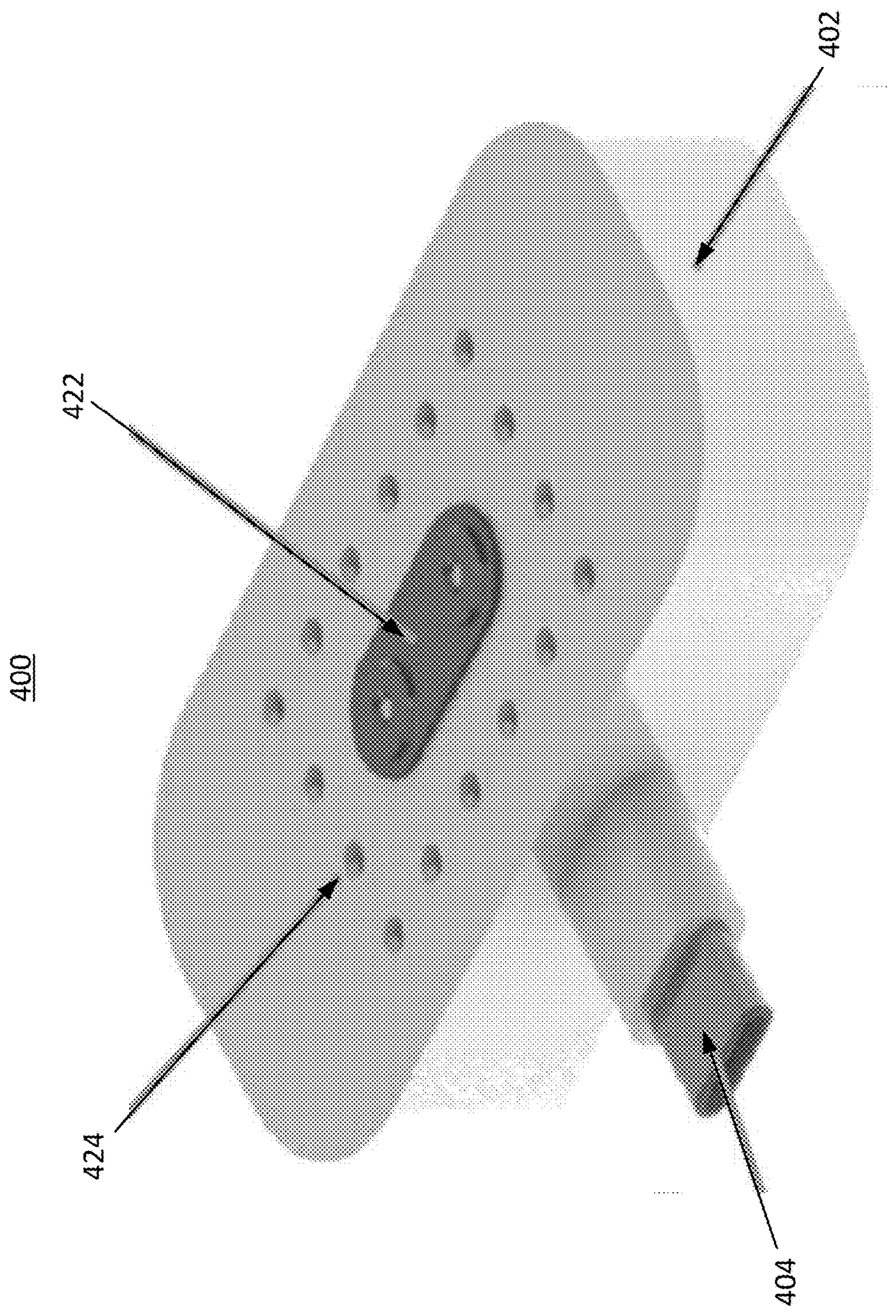
FIG. 4B is a perspective view of a second side of the vein detection device in FIG. 4A, according to an aspect of the disclosure.

An example of a vein detection device is shown in FIG. 4A as vein detection device 400. The vein detection device 400 includes main body 402 (e.g. made primarily of plastic) and optional data port 404 (e.g. mini universal serial data bus (USB), etc.) for insertion into a port of a mobile device (not shown). The mobile device may be a smart device such as a smartphone, tablet, or any handheld device that is provided with a screen to enable the user to view images captured and processed by vein detection device 400. The opposite side of vein detection device 400, shown in FIG. 4B, includes light sources 424 located on main body 402 and stereo cameras 422 including optional optical lenses for focusing (e.g. lens can provide autofocusing on the target vein). In use, the side of vein detection device 400 shown in FIG. 4B is placed at a distance from the skin of the patient. This distance is based on the focusing capabilities of the camera and any optical lenses used by detection device 400, and is generally set greater than the minimum focusing distance of the camera/lens configuration in order to capture a sharp and clear image. In one example, this distance may be greater than or equal to four times the focal length of the lens used. For a typical mobile device camera, this may be a few inches. In general, during operation, light sources 424 are activated to illuminate the skin, and stereo cameras 422 captures focused images of the illuminated skin layers and vein pattern.

Figure 4C:
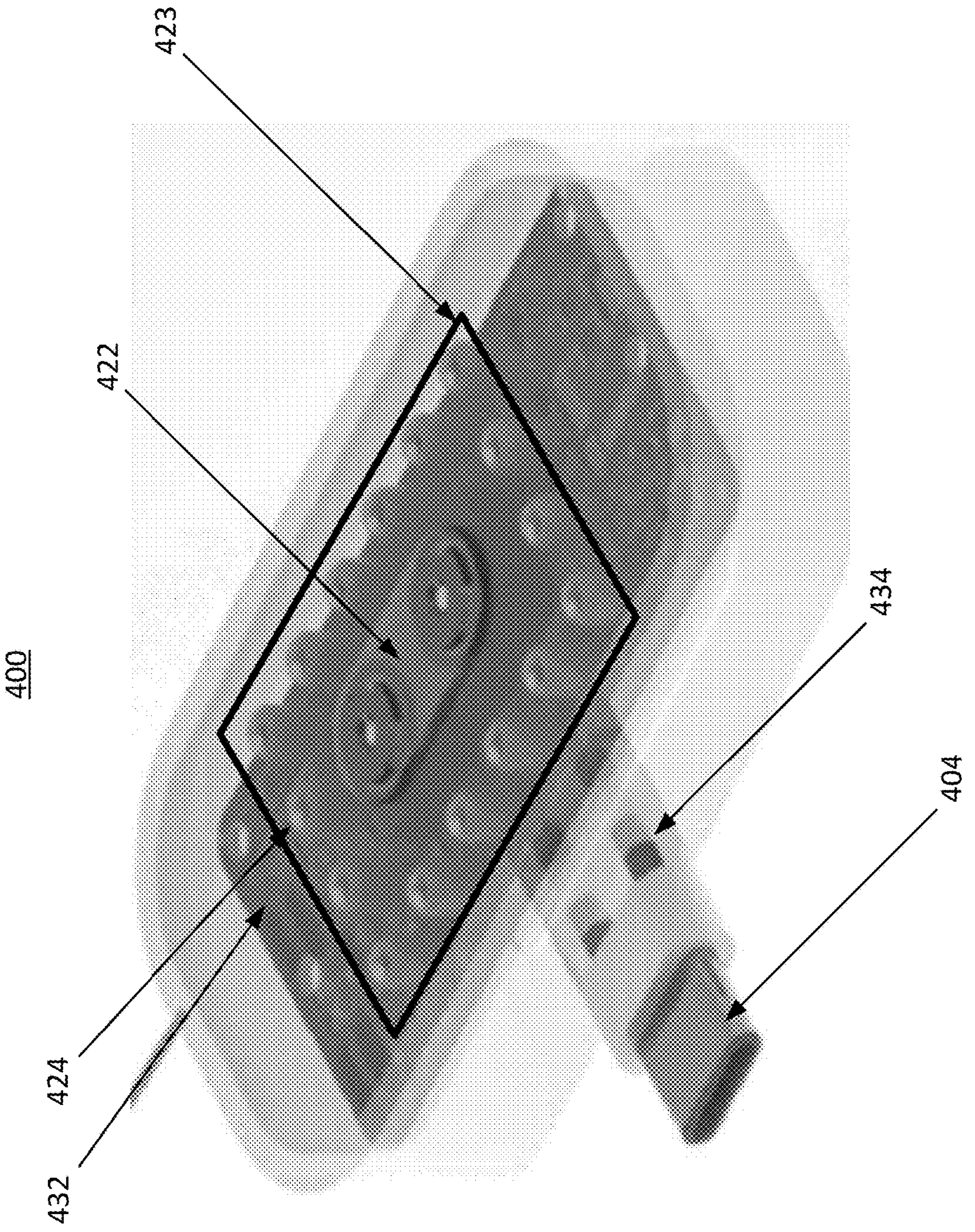
FIG. 4C is a transparent perspective view of the second side of the vein detection device in FIG. 4B, according to an aspect of the disclosure.

Main body 402 also includes various electronic components. These electronic components are shown in FIG. 4C. Specifically, light sources 424 (e.g. 750 nm LEDs) and stereo cameras 422 are mounted to printed circuit board 432 which includes, among other features, electronic components not shown such as a processor, memory and communication circuitry. The electronic components inside main body 402 are connected to data port 404 via wires 404. In addition to the electronic components, main body 402 may also include optical devices 423. These optical devices may include a band pass filter placed in front of stereo cameras 422 to eliminate ambient light, polarizers placed orthogonally over stereo cameras 422 and LEDs 424 to reduce specular reflection from the skin layers, as well as holographic diffusers placed over LEDs 424 to increase optical isotropy.

Figure 5:
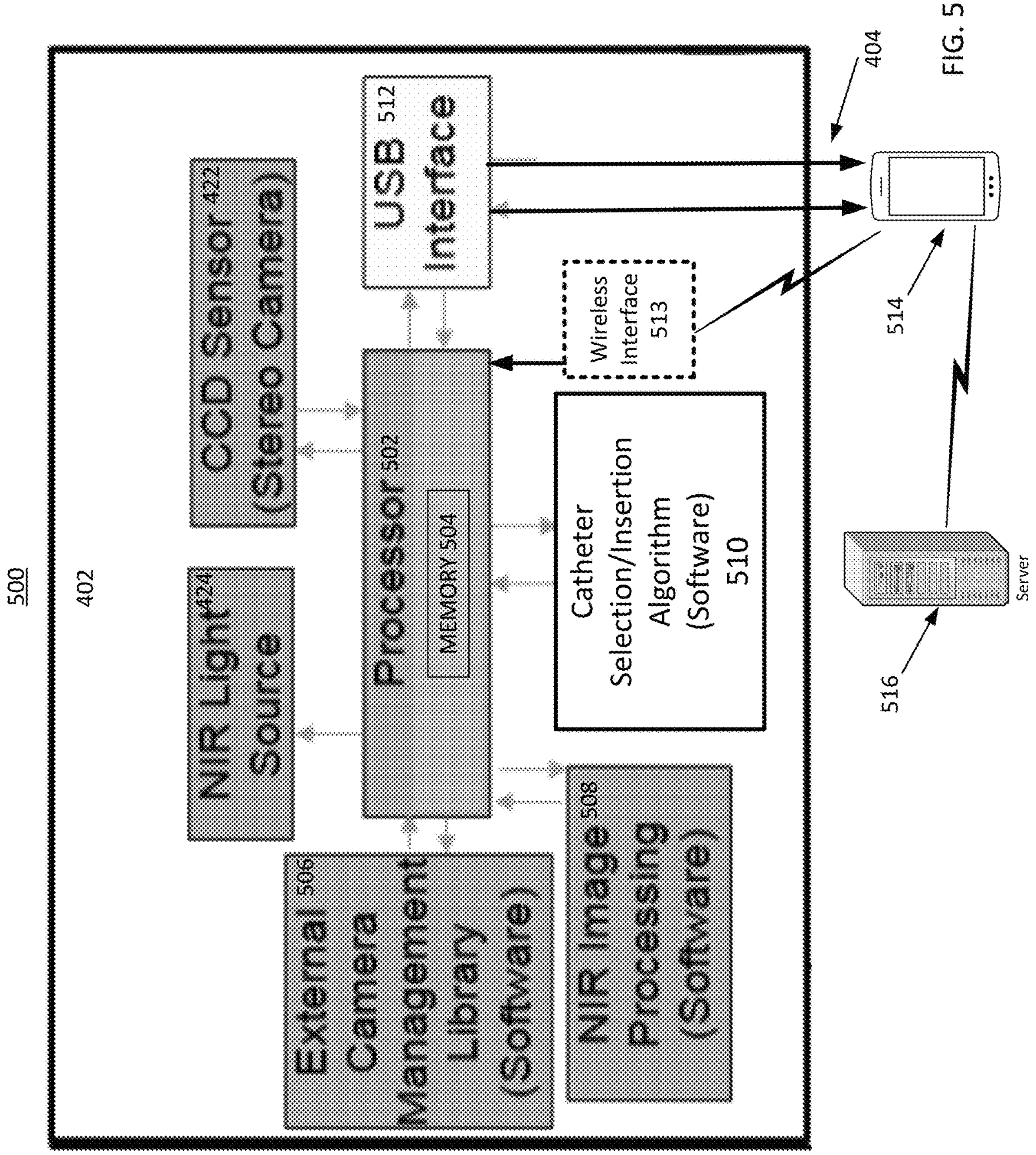
FIG. 5 is block diagram of the vein detection system, according to an aspect of the disclosure.

FIG. 5 is block diagram 500 showing the internal electronic components of the vein detection device 400 shown in FIG. 4C and the communication with the mobile device (e.g. smartphone) and a server. In this example, main body 402 of vein detection device 400 houses near infrared (NIR) light source(s) (e.g. NIR LEDs), stereo cameras (e.g. two CCD sensors) 422, processor 502 with memory 504, external camera management library 506, NIR image processing software 508, catheter selection/insertion software 510, optional USB interface 512 (or other equivalent wired data interface) and/or optional wireless (e.g. Bluetooth) interface 513.

During operation, vein detection device 400 is either plugged into mobile device (e.g. smartphone) 514 via optional data port 404, or connected wirelessly (e.g. Bluetooth Connection) to mobile device 514 via wireless interface 513. Once connected, the caregiver executes a vein detection application installed on mobile device 514. This application allows the caregiver to control vein detection device 400 via mobile device 514 (e.g. send/receive data to/from vein detection device 400), communicate with server 516 (e.g. send/receive data to/from server 516), as well as enter pertinent information (e.g. patient information, medical procedure information, etc.).

Figure 6A:
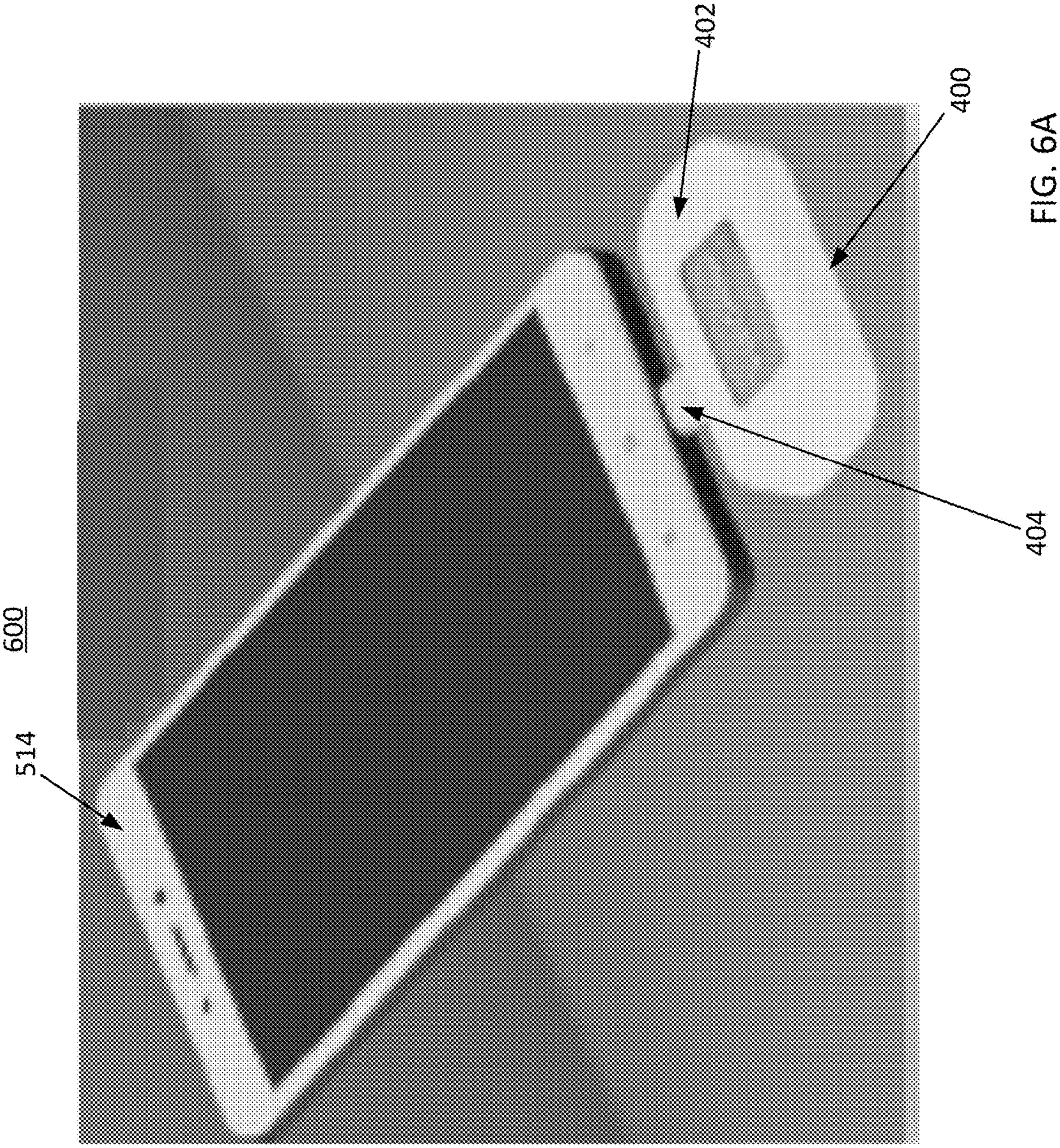
FIG. 6A is a perspective view of the vein detection device plugged into a mobile device, according to an aspect of the disclosure.

In one example, the caregiver (e.g. phlebotomist) connects (e.g. wired or wireless) mobile device 514 to vein detection device 400 (e.g. see 600 in FIG. 6A) and opens the vein detection application. The caregiver then enters (e.g. by way of manual entries, barcode scan, quick response (QR) code scan, etc.) patient information (e.g. patient ID) and other information (e.g. prescription) into mobile device 514. Mobile device 514 then instructs the caregiver to place vein detection device 400 at a distance from the target area (e.g. arm) of the patient. This distance is based on the focusing capabilities of the camera and any optical lenses used by detection device 400, and is generally set greater than the minimum focusing distance of the camera lens configuration in order to capture a sharp and clear image.

Vein detection device 400 may be held in place (e.g. on the target are of the patient) by the caregiver. Alternatively, vein detection device 400 may be held in place and stabilized by a holder, or affixed to the target area of the patient.

Figure 6B:
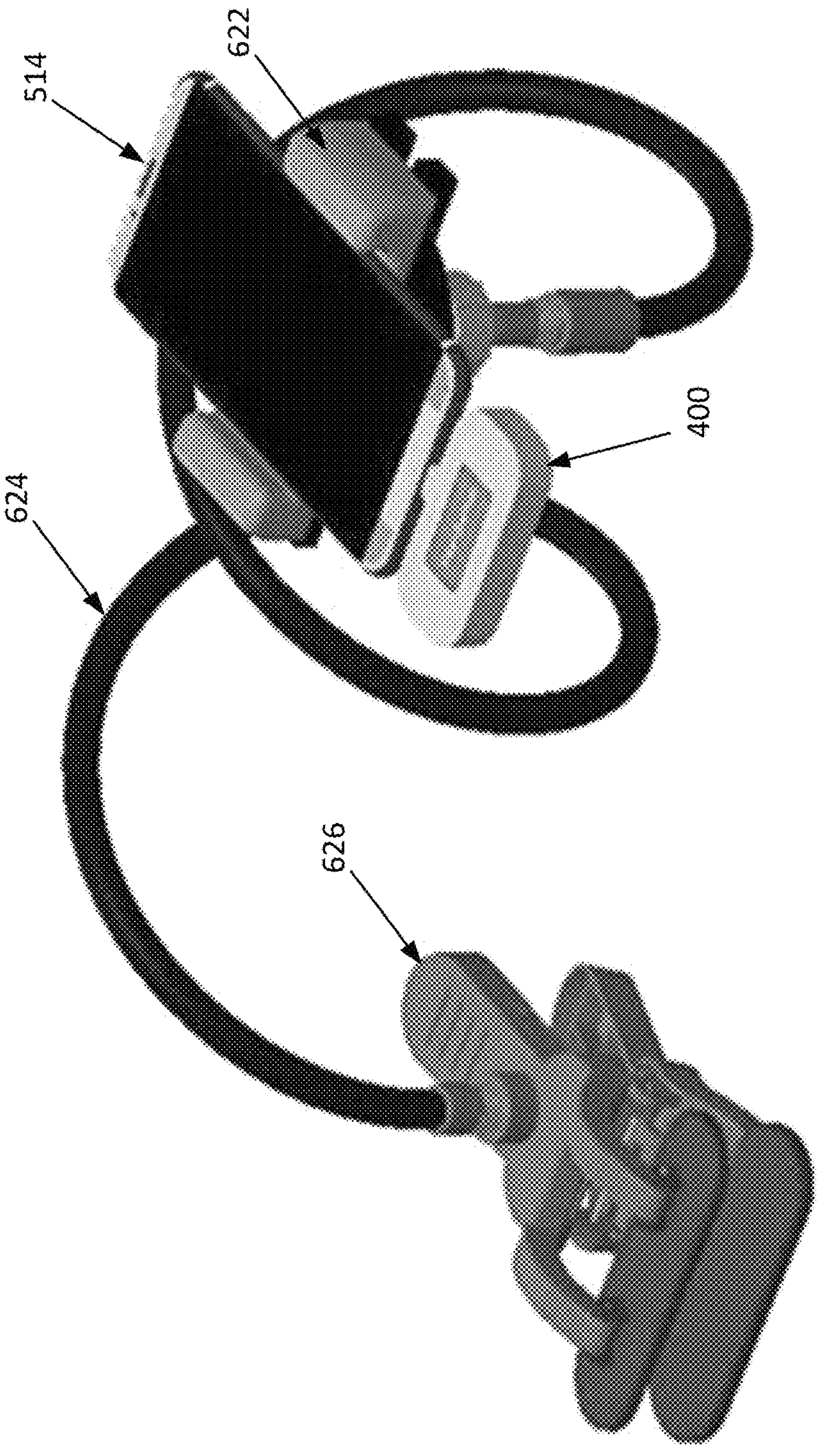
FIG. 6B is a perspective view of the vein detection device plugged into a mobile device that is stabilized by a clamped gooseneck holder, according to an aspect of the disclosure.

In one example, FIG. 6B shows a perspective view 620 of the vein detection device plugged into a mobile device that is stabilized by a clamped gooseneck holder that includes a mobile device holder 622, a gooseneck 624 (e.g. flexible jointed metal pipe) connected to mobile device holder 622 and a clamp 626 connected to gooseneck 624. During operation, the mobile device is held in place (e.g. under tension) by holder 622 and clamp 626 is clamped to a fixed surface (e.g. table, chair, etc.). Once clamp 626 is clamped to a fixed surface, gooseneck 624 may be adjusted (e.g. bent) by the caregiver such that vein detection device 400 is placed at a distance from the skin of the patient based on the focusing capabilities of the camera and any optical lenses used by detection device 400. The rigidity of gooseneck 624 stabilizes and holds vein detection device 400 in place at a set distance from the patient's skin for the vein scanning procedure. As mentioned above, this distance is based on the focusing capabilities of the camera and any optical lenses used by detection device 400, and is generally set greater than the minimum focusing distance of the camera lens configuration in order to capture a sharp and clear image.

Figure 6C:
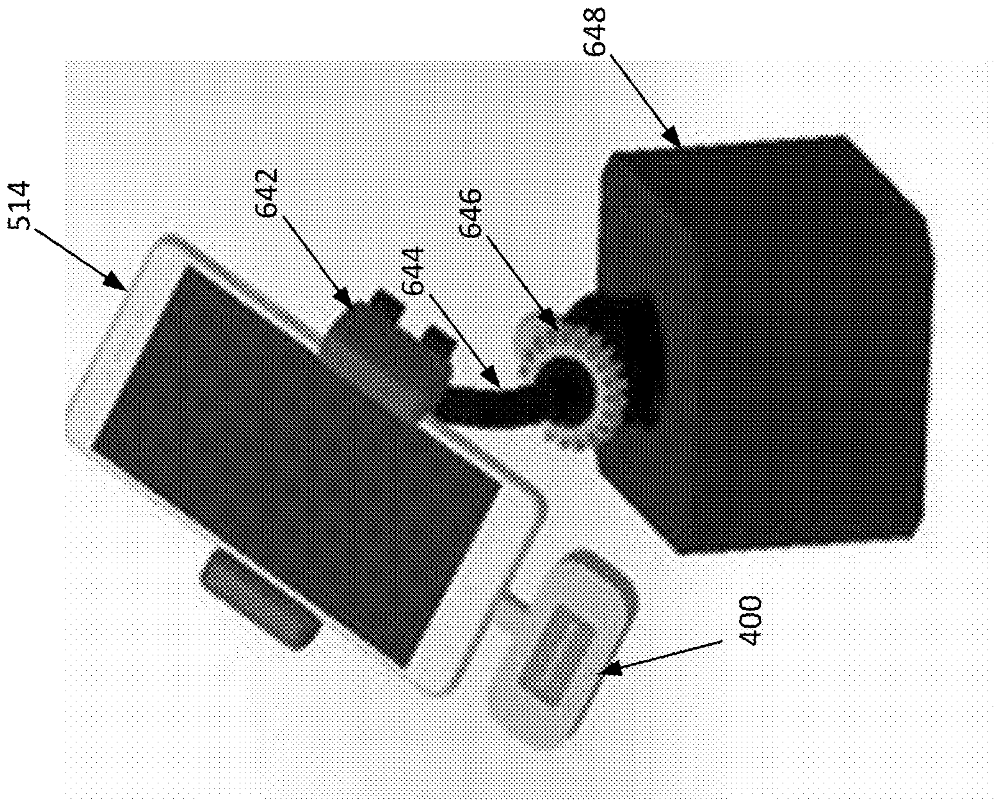
FIG. 6C is a perspective view of the vein detection device plugged into a mobile device that is stabilized by a block mounted gooseneck holder, according to an aspect of the disclosure.

In another example, FIG. 6C shows a perspective view 640 of the vein detection device plugged into a mobile device that is stabilized by a block mounted gooseneck holder that includes a holder 642, gooseneck 644 (e.g. flexible jointed metal pipe) connected to holder 642 and connected to block base 648 (e.g. weighted block) via adjustment ring 646 that sets an angle of gooseneck 644 relative to block base 648. During operation, the phone is held in place (e.g. under tension) by holder 642. Once the phone is held in place, gooseneck 644 may be adjusted (e.g. bent) and adjustment ring 646 may be adjusted (e.g. loosened/tightened) such that vein detection device 400 is positioned at a distance from the skin of the patient based on the focusing capabilities of the camera and any optical lenses used by detection device 400. Similar to FIG. 6B, the rigidity of gooseneck 644 stabilizes and holds vein detection device 400 in place at a set distance from the patient's skin for the vein scanning procedure. As mentioned above, this distance is based on the focusing capabilities of the camera and any optical lenses used by detection device 400, and is generally set greater than the minimum focusing distance of the camera lens configuration in order to capture a sharp and clear image.

Figure 6D:
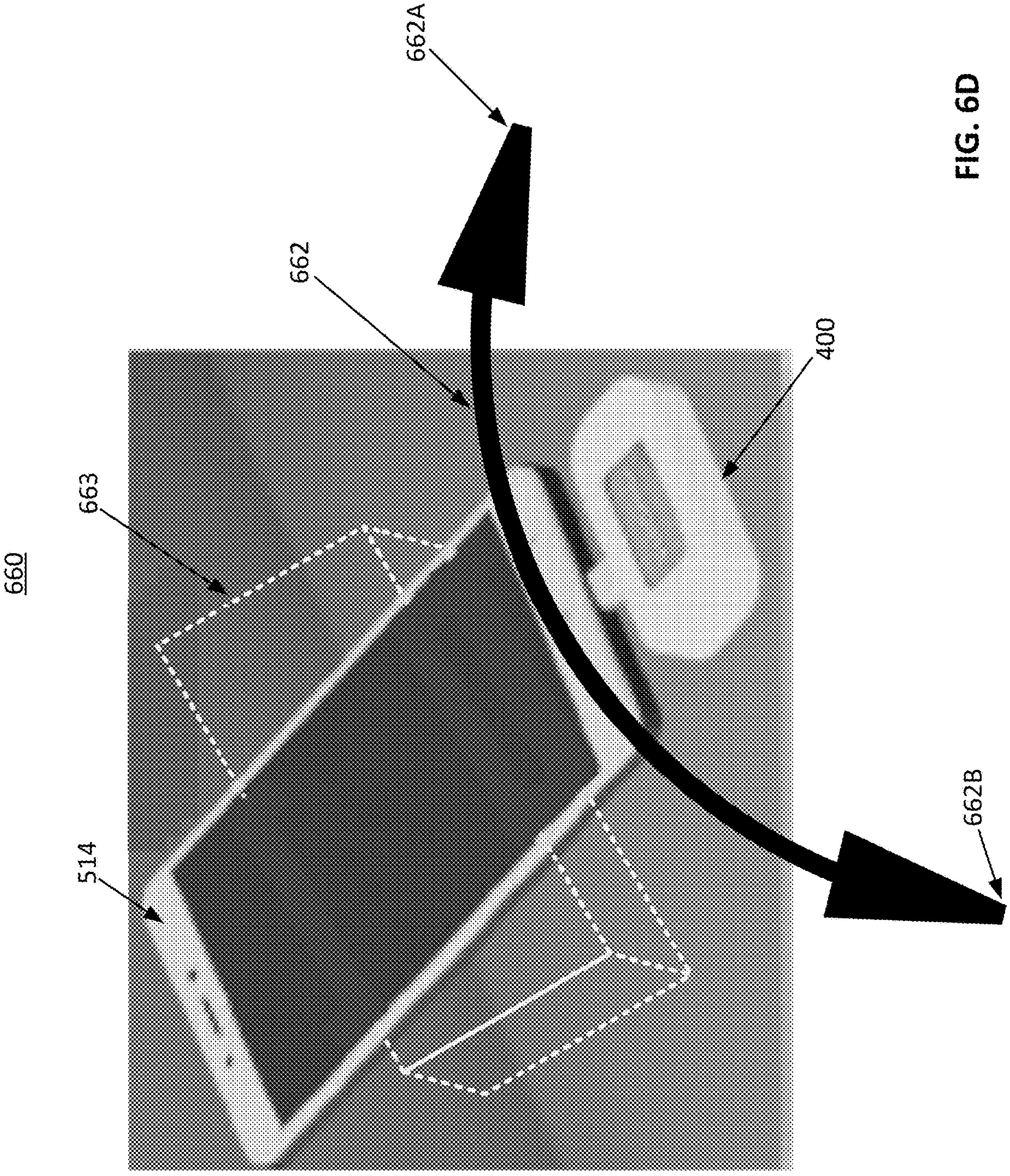
FIG. 6D is a perspective view of the vein detection device plugged into a mobile device that is stabilized by a strap, according to an aspect of the disclosure.

In yet another example, FIG. 6D shows a perspective view 660 of the vein detection device affixed by a strap 662. During operation, the caregiver positions the vein detection device 400 at a distance from the skin of the patient. This distance may be accomplished by use of a spacer 663 positioned in between vein detection device 400 and the user's arm. The caregiver then affixes the vein detection device 400 and spacer 663 to the target area by wrapping strap 662 (e.g. cloth or the like) around the patient (e.g. around the arm) and connecting strap end 662A to strap end 662B (e.g. ends may be Velcro or the like). Strap 662 and spacer 663 stabilizes and holds vein detection device 400 in place at a set distance from the patient's skin for the vein scanning procedure. As mentioned above, this distance is based on the focusing capabilities of the camera and any optical lenses used by detection device 400, and is generally set greater than the minimum focusing distance of the camera lens configuration in order to capture a sharp and clear image. Thus, the dimensions (e.g. thickness) of spacer 663 may be set according the focusing capabilities of the camera and optical lenses of detection device 400. The dimensions of spacer 663 may also be adjustable to accommodate the focusing capabilities of detection devices with different cameras and/or lenses.

Once vein detection device 400 is positioned, mobile device 514 instructs processor 502 of the vein detection device to perform vein detection. Specifically, processor 502 turns on NIR light source(s) 424 to illuminate the target area of the patient's skin and turns on stereo cameras 422 with the aid of external camera management library 506 to capture stereo still images or stereo video of the illuminated target area. Processor 502 also executes NIR image processing algorithm 508 stored in memory 504 which performs image processing on the captured stereo images/video. In general, NIR image processing algorithm 508 extracts relevant features (e.g. points on the illuminated target vein) in the captured images/video and reconstructs a 3D image of the target vein using triangulation techniques. Processor 502 also executes catheter selection/insertion software 510 which analyzes the reconstructed 3D vein image to select an appropriate catheter (e.g. appropriate needle size), an appropriate insertion site and an appropriate insertion angle for the needle insertion procedure. The 3D reconstructed image and the catheter information are then relayed to mobile device 514 via USB interface 512 or wireless interface 513 and displayed on mobile device 514 for the caregiver.

Although not shown, vein detection device 400 may also be able to mark or aid in the marking of the insertion site on the patient's skin. In one example, vein detection device 400 may have a marking arrow that allows the caregiver to mark (e.g. using an ink marker), the insertion site on the patient's skin. The caregiver can then remove vein detection device 400 and insert the catheter needle in the marked location. In another example, vein detection device 400 may include a marking window (e.g. circular opening) that allows the caregiver to insert the catheter while vein detection device 400 is still positioned at the distance from the target area on the patient's skin. Any such marking window may be located on the perimeter of body 402 or in the central portion of body 402. In one example, processor 502 may relay instructions to mobile device 514 instructing the caregiver in accurately aligning the marking arrow/window with the appropriate insertion site. In another example, caregiver (e.g. based on experience) may manually select and mark the insertion site based on the displayed 3D image.

Optional server 516 may also aid in the vein detection process. For example, server 516 may send patient information (e.g. patient age, weight, ID, previous injection results, injection site recommendations, etc.) to mobile device 514 in order to more accurately control vein detection device 400. Likewise, mobile device 514 may send analysis and injection results (e.g. injection success/failure, etc.) back to server 516 to update the patient's profile and medical history. Such information may then be used to update the NIR image processing software and/or the catheter selection software.

Figure 7:
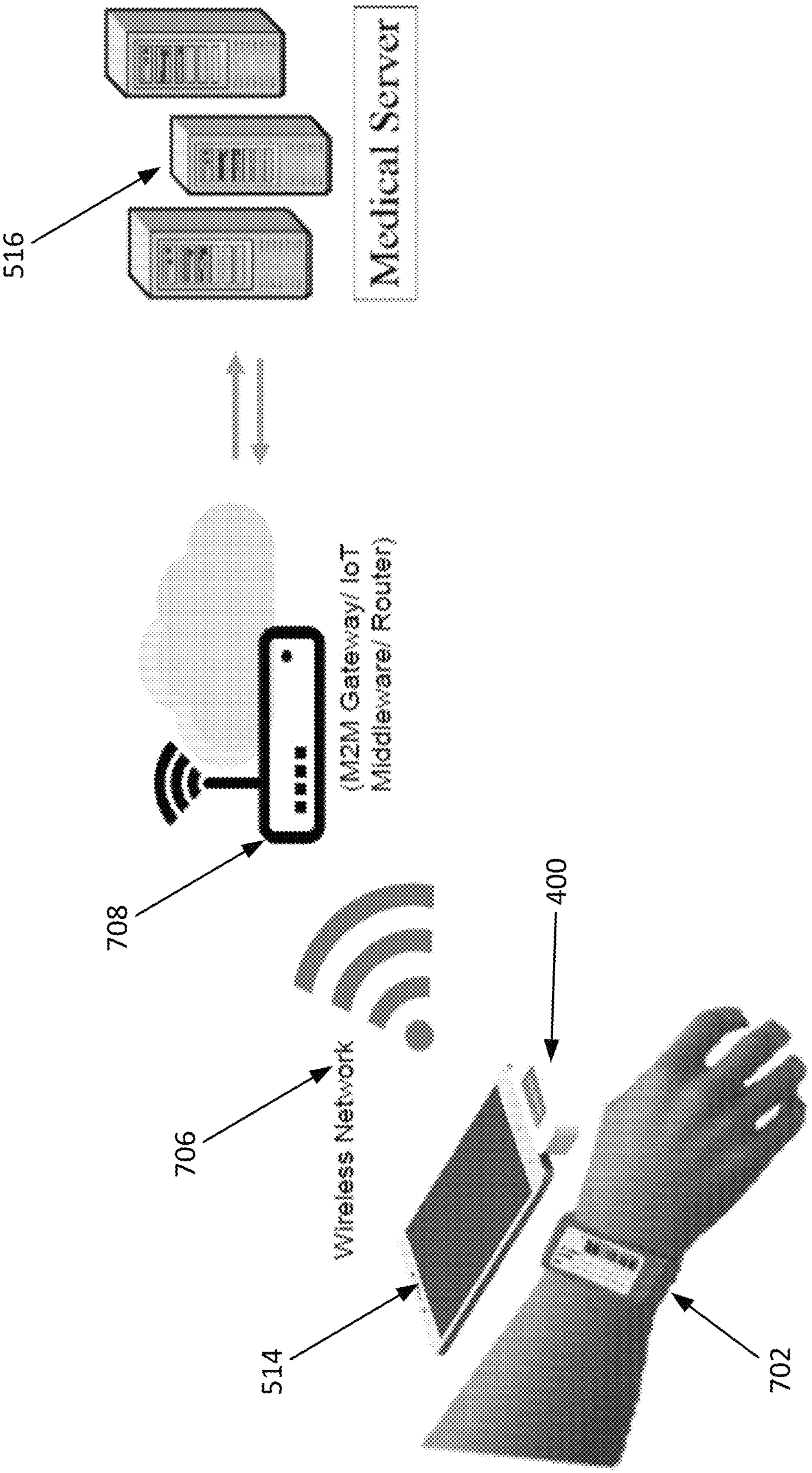
FIG. 7 is a communication flow diagram of the vein detection system, according to an aspect of the disclosure.

FIG. 7 shows an example of a communication flow diagram 700 between the vein detection device 400 and other devices in the vein detection system. As described above, the vein detection system may include vein detection device 400 connected (e.g. wired or wirelessly) to mobile device 514 and to medical server 516 via wireless (e.g. WiFi) hardware such as gateway/router 708. In addition, the vein detection system may include a patient bracelet 702 that includes a barcode, QR code, RFID chip, etc. that is scanned by either the mobile device 514 or the vein detection device 400 to identify the patient and retrieve pertinent patient/procedure information from server 516.

For example, during operation, the caregiver may capture, via a camera (not shown) on mobile device 514, or via the stereo cameras 422 on vein detection device 400 an image of patient bracelet 702. Mobile device 514 may analyze the code on bracelet 702 to determine an identification number. Mobile device 514 may then send this identification number to server 516 (e.g. medical server) via wireless network 706 and gateway/router 708. Server 516 may retrieve pertinent patient information (e.g. patient ID, medical history, etc.), and procedure information (e.g. prescription information). This retrieved information is then sent back to mobile device 514 via gateway/router 708 and wireless network 706. Upon receiving the retrieved information, mobile device 514 instructs vein detection device 400 to perform the vein detection and the catheter selection/insertion algorithm based in part on the retrieved information. The camera on mobile device 514, or the stereo cameras on vein detection device 400 may also be used to scan bar codes and QR codes on the packaging of a medical device such as an intravenous catheter device, on a medication label, or on a patient's medical charts. The process for retrieving information (e.g. patient information, procedural information, prescription information, etc.) from server 516 based on the bar codes and QR codes is similar to the retrieval process described above with respect to bracelet 702.

Image Processing

Figure 8A:
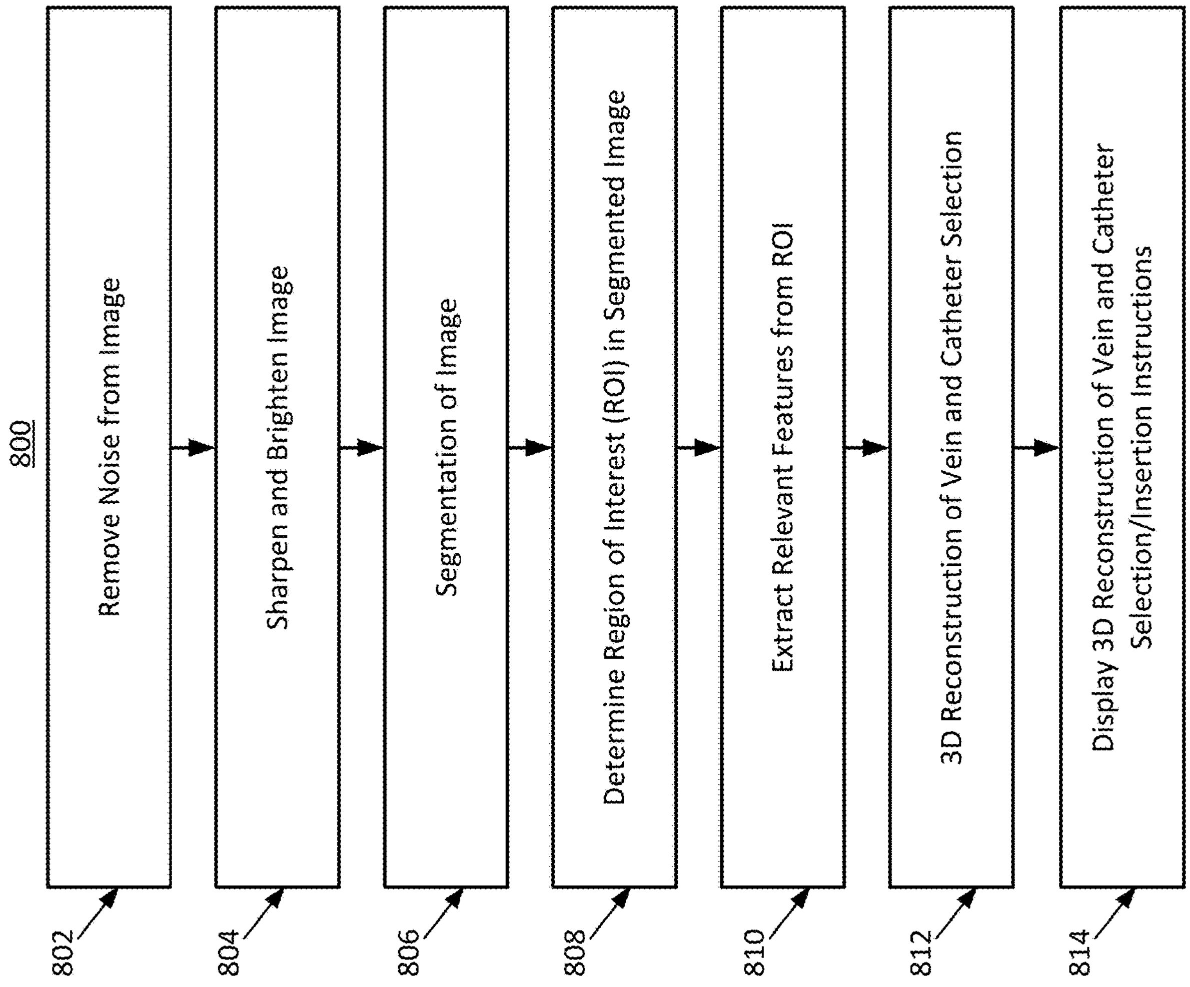
FIG. 8A is a flowchart showing an image processing technique of the vein detection system, according to an aspect of the disclosure.

As described above, vein detection is performed by illuminating the target area (e.g. subcutaneous layer in patient's arm) with NIR light, capturing stereo images, and reconstructing a 3D image of the detected vein. FIG. 8A is a flowchart 800 showing an example of an image processing technique 800 for performing these operations.

In steps 802-812, processor 502 executes NIR image processing 508. Specifically, in step 802, processor 502 removes noise from the captured stereo images. This may be performed via low pass mask filtering of the pixels or the like. In step 804, processor 502 then sharpens and/or brightens the captured stereo images. This may be performed via high pass mask filtering of the pixels or the like. In step 806, the filtered stereo images are segmented such that the processor 502 can determine a region of interest (ROI) in step 808 (e.g. a segment of the image containing the destination vein). Once the ROI is identified, in step 810, processor 502 extracts relevant features (e.g. various points along the vein). In step 812, processor 502 performs a 3D reconstruction of the vein and determines the appropriate type of catheter to use, insertion site, and insertion angle based on the extracted points. As described above, the 3D reconstruction of the vein in step 812 is performed based on 3D coordinates and triangulation techniques of the extracted points in the stereo images. Once the 3D reconstruction and catheter selection/insertion algorithm is complete, the 3D image and catheter information is displayed as output on mobile device 514 in step 814.

Figure 8B:
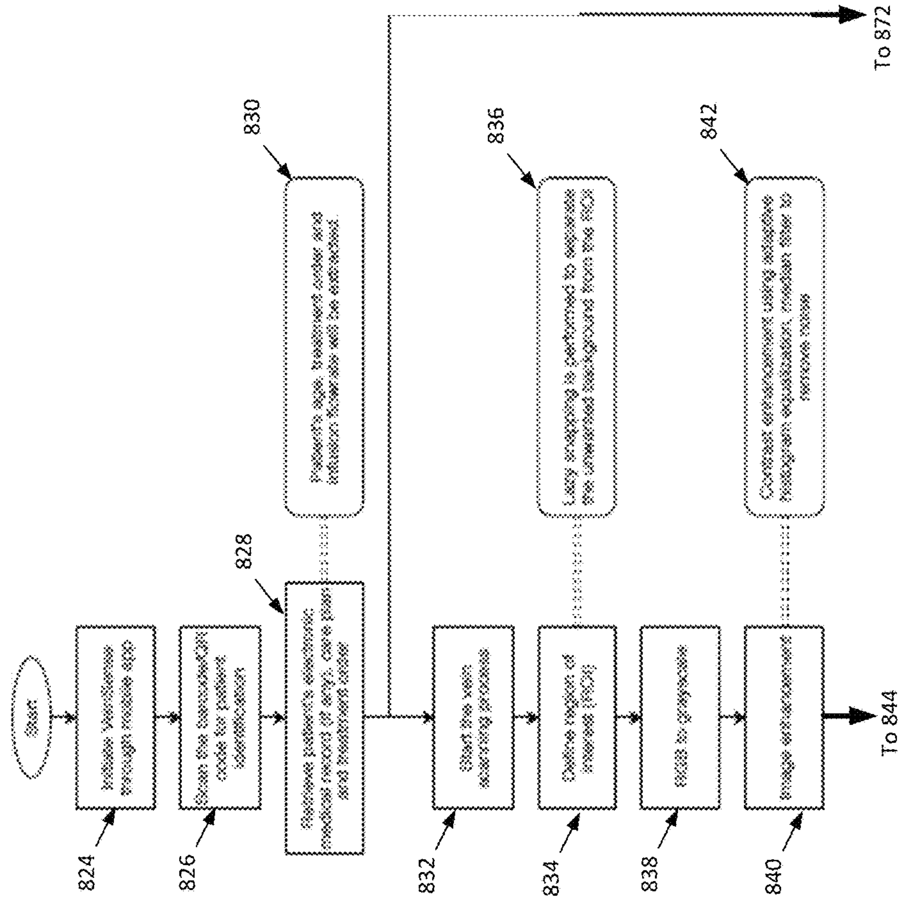
FIG. 8B is another flowchart showing an image processing technique of the vein detection system, according to an aspect of the disclosure.
Figure 8C:
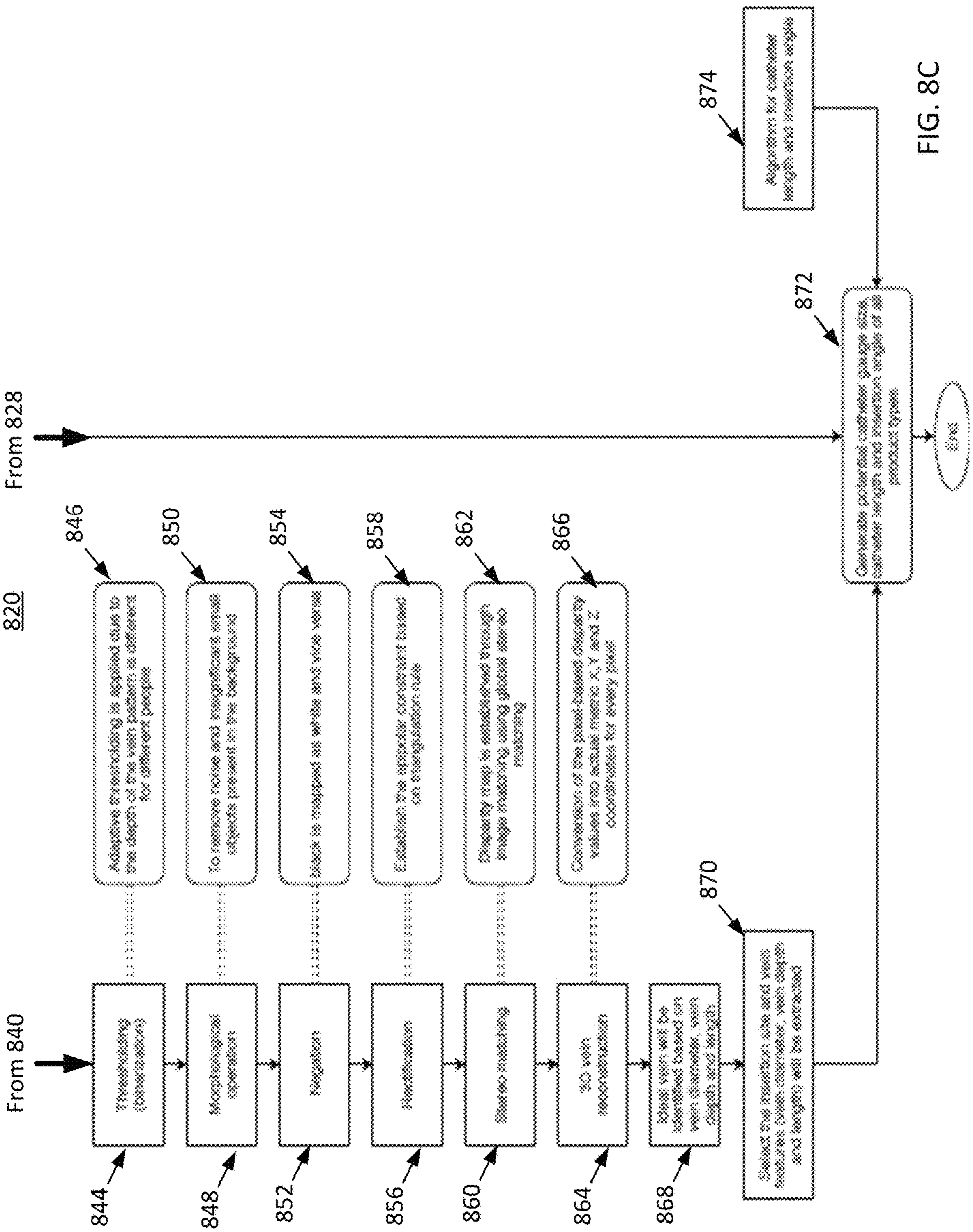
FIG. 8C is a continuation of the flowchart in FIG. 8B showing the image processing technique of the vein detection system, according to an aspect of the disclosure.

FIGS. 8B and 8C depict another flowchart 820 showing more details of the image processing technique of the vein detection system. In step 824 (see FIG. 8B), the caregiver initiates the vein detection system through the mobile software application on mobile device 514 which instructs the caregiver to input patient identification information, for example, by scanning a bar/QR code associated with the patient (step 826). In steps 828/830, the mobile device 514 connects to medical server 516 to retrieve any available patient medical records such as care plan and treatment order. For example, patients age, weight, treatment order and infusion flowrate may be retrieved. After vein detection device 400 is placed at the target area, in step 832, processor 502 instructs camera 422 to scan the target area for veins. In steps 834/836, processor 502 analyzes the captured image and performs techniques such as lazy snapping (e.g. image cutout) to separate unwanted background detail from the veins to define a region of interest (ROI). In step 838, processor 502 may convert the image from the red, green, blue (RGB) color model to grayscale. In steps 840/842, processor 502 performs image enhancement by using techniques such as adaptive histogram equalization and filtering to remove noise. In steps 844/846 (see FIG. 8C), processor 502 performs binarization of the image by using techniques such as adaptive thresholding due to different depths of the vein pattern. In steps 848/850, processor 502 performs morphological operations to remove noise and insignificant small objects from the background of the image. In steps 852/854, processor 502 performs rectification (e.g. projecting the image onto a common image plane) by establishing an epipolar geometrical constraint based on triangulation. In steps 860/862, processor 502 performs stereo matching to establish a disparity map (e.g. stereo image). In steps 864/866, processor 502 performs 3D vein reconstruction by converting the pixel-based disparity values into 3D X, Y and Z coordinates for every pixel. In step 868, processor 502 identifies the optimal vein from the 3D image based on vein diameter, depth and length. In step 870, processor 502 determines the vein insertion site, and in steps 873/874 generates a potential catheter gauge, size, length and insertion angle with the aid of an algorithm for catheter length and insertion angle (see FIG. 9C for an example of the algorithm). This information is then displayed to the caregiver on the screen of the mobile device (see FIGS. 9A and 9B for examples of the displayed information).

Thus far, the processing of stereo images, 3D reconstruction of the vein, and the catheter selection/insertion algorithm have been described as being performed by vein detection device 400. This processing may alternatively be performed by the mobile device 514, the server 516, or any combination of the mobile device, server and vein detection device 400 in order to share the computation load. For example, vein detection device 400 may simply send the captured stereo images to mobile device 514 which then processes the stereo images, performs 3D reconstruction of the vein, and performs the catheter selection/insertion algorithm with or without the aid of server 516. Such a load sharing configuration would result in reduced size and cost of vein detection device 400.

Software Application

As described above, the 3D reconstructed image and catheter information is displayed on mobile device 514 in order to aid the caregiver in performing a successful catheter insertion. More specifically, this information is displayed as part of a vein detection application being executed on mobile device 514.

Figure 9A:
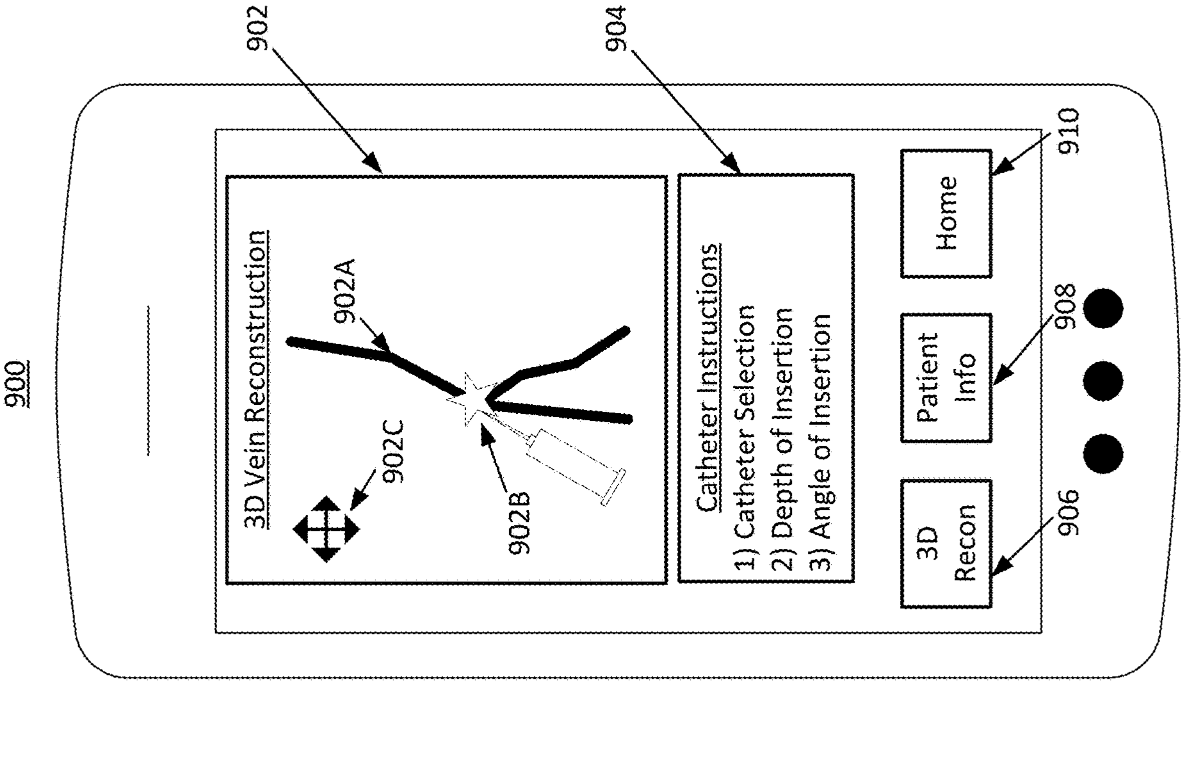
FIG. 9A is a view of a software application interface of the vein detection device, according to an aspect of the disclosure.

An example of how the vein detection application may display this information is shown in the software application interface 900 of FIG. 9A. In this example, the mobile device display may include the 3D vein reconstruction 902 showing the vein 902A, the insertion sight 902B, catheter instructions 904 (e.g. catheter type selection, catheter gauge/length selection, depth of insertion, angle of insertion, etc.) as well as arrows 902C instructing the caregiver on how the vein detection device should be moved in a specific direction with respect to the target location (e.g. adjusted on the patient's arm to better located the vein). In addition, mobile device display may also include soft buttons that allow the caregiver to control the vein detection process. For example, the 3D reconstruction button 906 may be pressed to start/stop the 3D reconstruction process. The patient information button 908 may be pressed to retrieve patient information from the server or to enter patient information into the system. The home button 910 may be pressed to return to the home screen of the vein detection application. In general, the vein detection application provides the caregiver with information beneficial to performing a successful catheter needle insertion.

Figure 9B:
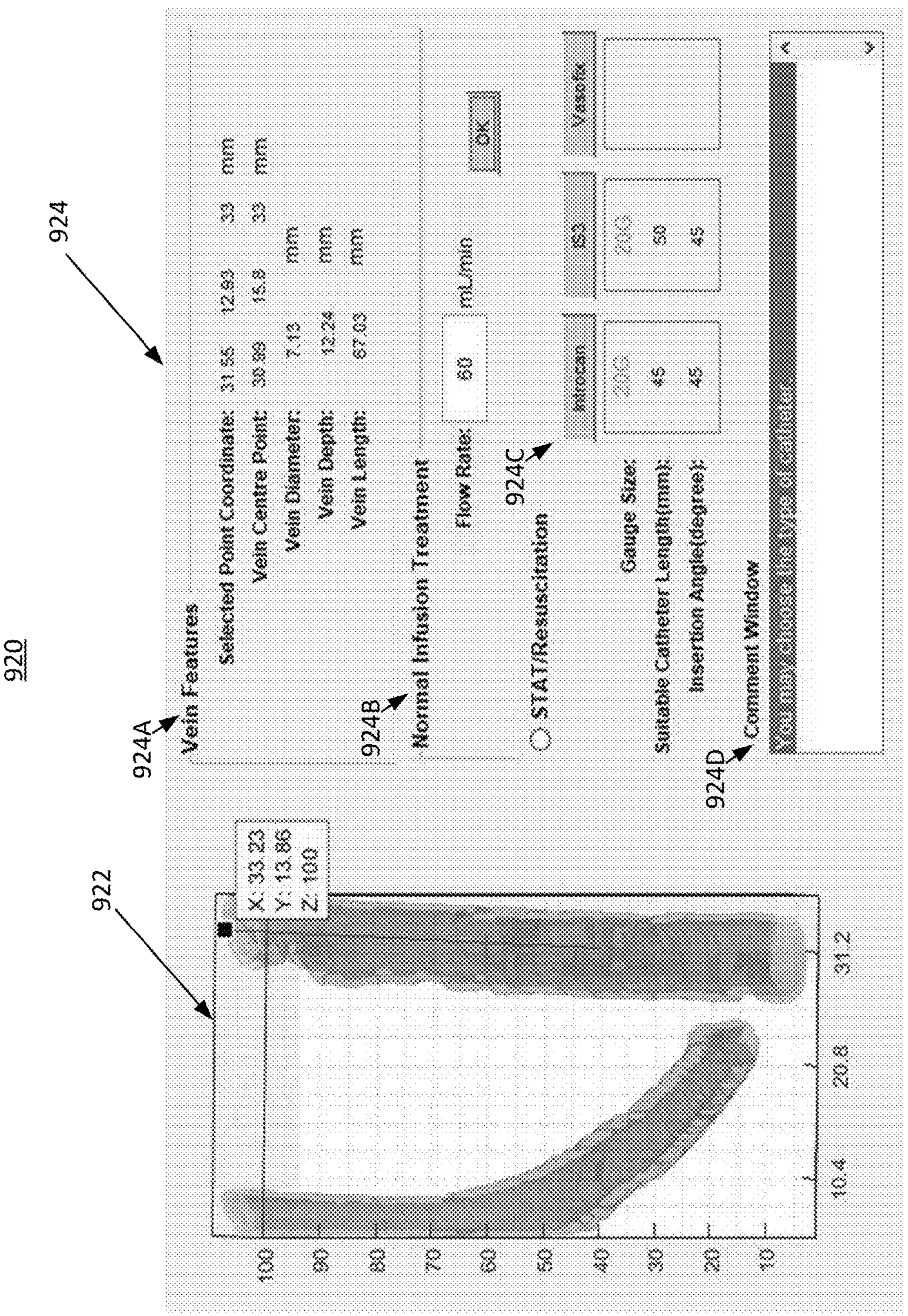
FIG. 9B is a view of another software application interface of the vein detection device, according to an aspect of the disclosure.

FIG. 9B is a view of another software application interface 920 of the vein detection device. In this example, the mobile device display includes numerical data 924A, 924B and 924C representing vein feature data (e.g. insertion point), infusion treatment data (e.g. flowrate and catheter selection). The mobile device display may also include an optional comment window 924D for allowing the caregiver to record notes and feedback (e.g. insertion failure/success, etc.). In addition, the mobile device display may display the 3D vein reconstruction 922.

Figure 9C:
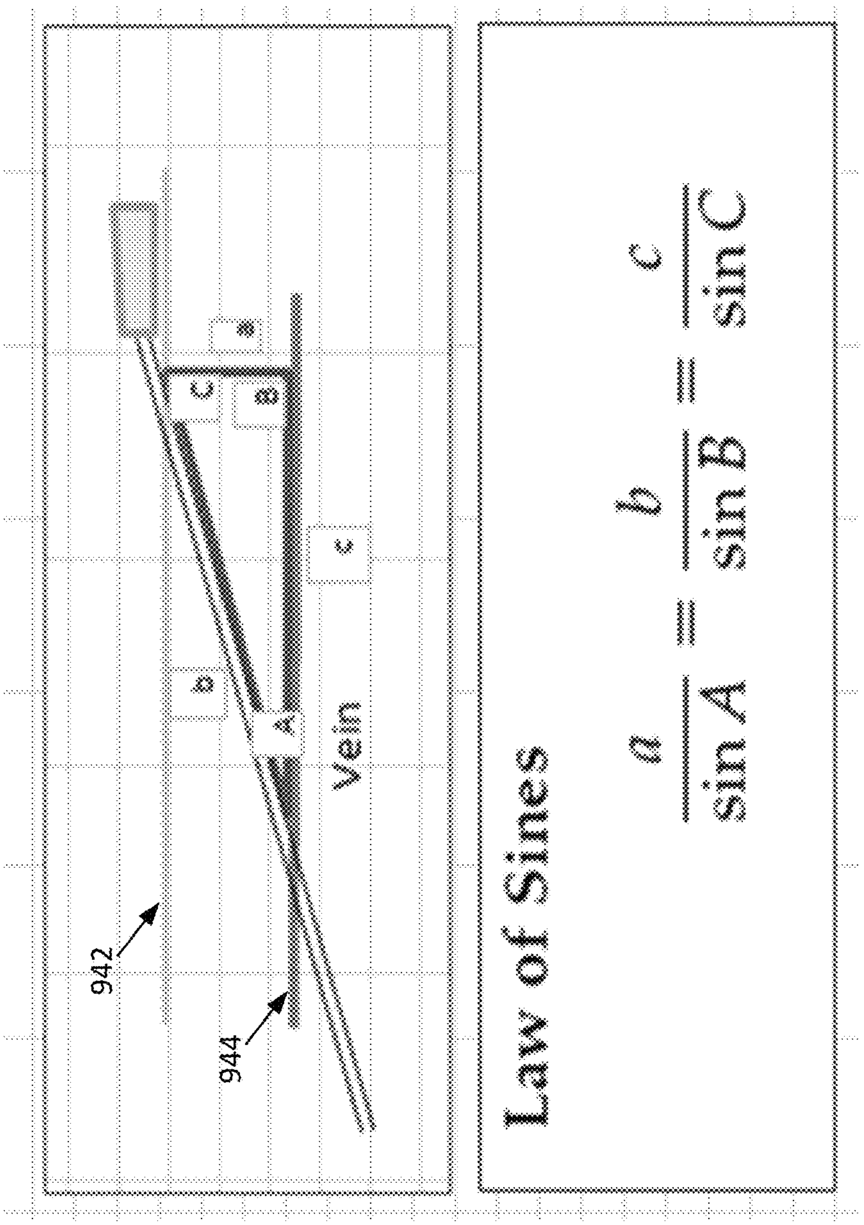
FIG. 9C is a view of an algorithm executed by the vein detection device to determine catheter length and insertion angle, according to an aspect of the disclosure.

The catheter length and insertion angle shown in 924C of FIG. 9B and step 874 of FIG. 8C may be determined by geometrical angles and distances from the patient's skin 942 to the target vein 944 as shown in schematic 940 of FIG. 9C. For example, in a side view of the 3D image, a triangle with sides 'a', 'b' and 'c' and angles 'A', 'B' and 'C' may be drawn between skin surface 942 and target vein 944. Side 'b' (the hypotenuse) of the triangle indicates a minimum length of the catheter and angle 'C' indicates the suggested insertion angle of the catheter.

Operational Example

Figure 10:
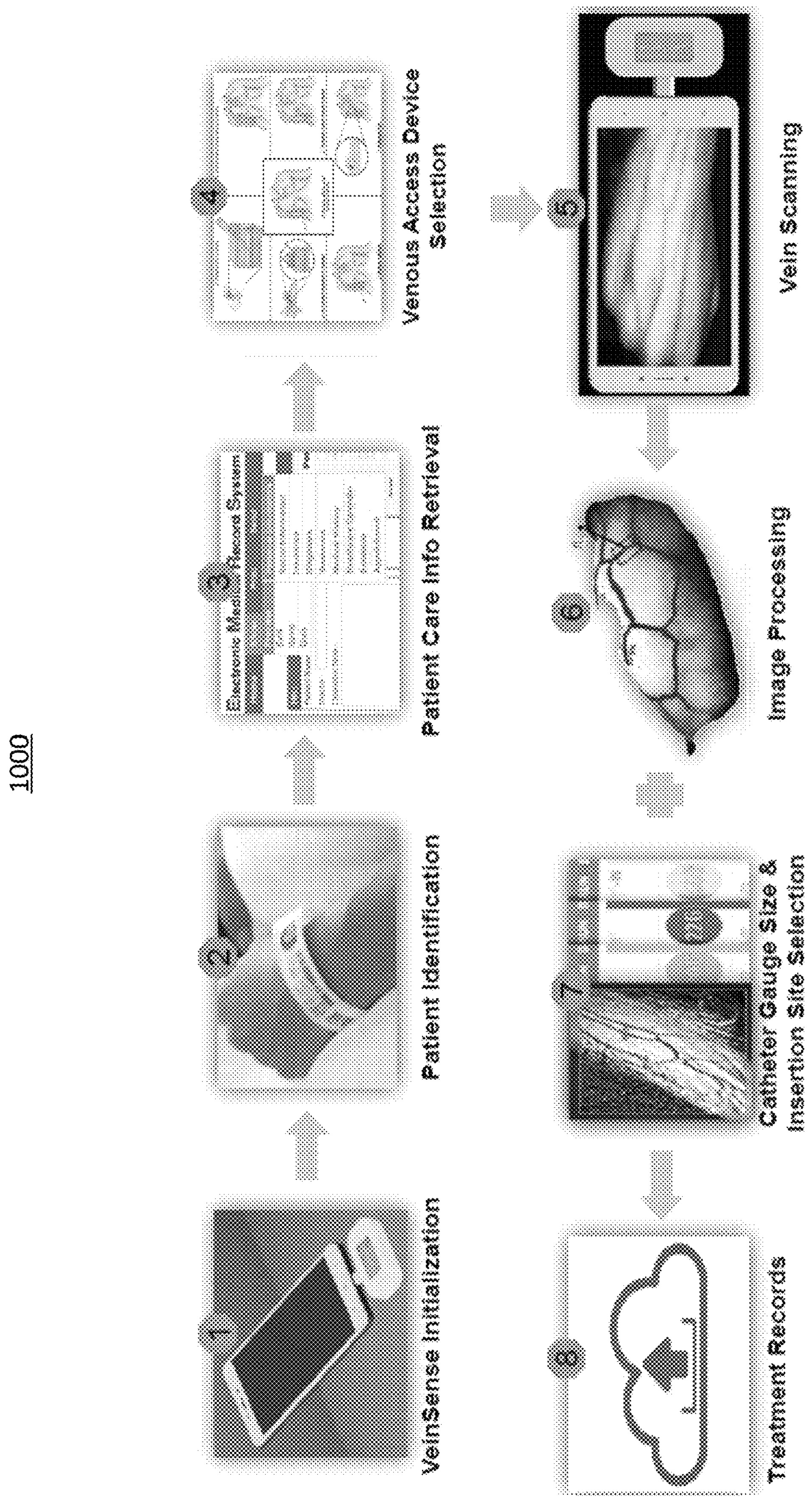
FIG. 10 is flowchart showing the operation of the vein detection system, according to an aspect of the disclosure.

FIG. 10 is flowchart 1000 showing an overall operational example of the system. In step 1, vein detection device 400 is connected (e.g. physically plugged in or wirelessly connected) to mobile device 514 and initialized. The initialization may be performed by opening the vein detection application on mobile device 514. After initialization, the patient is identified in step 2. This may be performed by manually entering the patient information into mobile device 514 or using the camera of mobile device 514 to capture an image of a barcode or QR code associated with the patient (e.g. printed on a piece of paper, printed on a wristband, displayed on the patient's mobile device, etc.). Once the patient is identified, mobile device 514 retrieves patient care information from server 516 which may be a medical server operated by a hospital. Server 516 retrieves patient information (e.g. patient name, patient age, patient weight, medical history, etc.) and procedure information (e.g. prescription with blood withdrawal instructions). In step 4, mobile device 514 may then instruct the caregiver on the selected target location (e.g. arm, hand, neck, etc.) for drawing the blood. Upon receiving the selected target location the caregiver places vein detection device 400 on the target location. Vein detection device 400 may be held in place by the caregiver or affixed (e.g. strapped) to the target area. In step 5, vein detection device 400 scans the target area by illuminating the target area with NIR light sources and capturing stereo images of the illuminated target area. In step 6, vein detection device 400 performs image processing to determine a ROI, extract features from the ROI and construct a 3D image of the vein. In addition, in step 7, vein detection device 400 uses the extracted features of the vein to select an appropriate catheter (e.g. size), insertion sight and insertion angle. Once the caregiver completes the catheter needle insertion, the caregiver may also input feedback to the mobile device such as success/failure of the insertion. This information (e.g. catheter information, success/failure of insertion, etc.) is then sent to server 516 to update the patient's medical records. These records may then be used to aid in future catheter insertions for the patient and for other patients.

CONCLUSION

The steps in FIGS. 8-10 may be performed by the vein detection device, the phone, the server, or a combination thereof as shown in FIG. 7, upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. In one example, data are encrypted when written to memory, which is beneficial for use in any setting where privacy concerns such as protected health information is concerned. Any of the functionality performed by the computer described herein, such as the steps in FIGS. 8-10 may be implemented in software code or instructions which are tangibly stored on a tangible computer readable medium. Upon loading and executing such software code or instructions by the computer, the controller may perform any of the functionality of the computer described herein, including the steps in FIGS. 8-10 described herein.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The invention claimed is:

1. A vein detection device comprising:

a light source operating at a wavelength for penetrating skin of a patient;

a stereo camera operating at the wavelength;

a communication interface configured to connect to a mobile device; and
a processor configured to:
retrieve from a medical server, via the communication interface, patient information associated with the patent including previous injection sites and previous injection results,
generate a target location on the patient for a new injection based on the patient information prior to illuminating the patient using the light source,
instruct a user of the vein detection device to illuminate the target location on the patient,
control the light source to illuminate the target location of the skin,
control the stereo camera to capture an image in the illuminated target location,
process the captured image to detect a vein of the patient illuminated by the light source,
reconstruct a three-dimensional image of the detected vein based on the patient information and the processed captured image,
transmit the three-dimensional image of the detected vein to the mobile device via the communication interface, and
following the new injection of the patient, transmit injection results associated with the new injection to the medical server for updating the previous injection sites and previous injection results stored in the patient information.

2. The vein detection device according to claim 1, wherein the vein detection device comprises a housing, an interchangeable adaptor protruding from the housing for insertion into a port of the mobile device constituting a smartphone, and the cameras of the stereo camera and the light source being disposed on a same side surface of the housing.

3. The vein detection device according to claim 1, wherein the processor is configured to instruct the server, via the communication interface, to store the reconstructed three dimensional image of the detected vein.

4. The vein detection device according to claim 1,
wherein the processor is further configured to select an insertion point for a catheter and dimensions of the catheter based on physical characteristics of the detected vein in the three-dimensional image, and transmit the selected insertion point to the mobile device.

5. The vein detection device according to claim 1,
wherein the operating wavelength of the light source and the stereo camera is in the near infrared (NIR) spectrum.

6. The vein detection device according to claim 1,
wherein the processor is further configured to instruct the user of the vein detection device to adjust an orientation of the vein detection device while capturing the image.

7. The vein detection device according to claim 1,
wherein the processor is further configured to reconstruct the three dimensional image of the detected vein by determining a region of interest (ROI), extracting relevant vein features from the ROI and performing 3D point cloud reconstruction of the relevant vein features.

8. The vein detection device according to claim 1, wherein the mobile device is a smartphone.

9. The vein detection device according to claim 1,
wherein the vein detection device or the mobile device is configured to capture an image of a code on a packaging of a catheter device, on a medication label, on a patient's medical charts or on a patient's wrist band, and
wherein the mobile device is configured to use the code to retrieve information relating to at least one of the patient, the catheter device, and the medication.

10. A vein detection method comprising:
identifying a patient;
retrieving from a medical server, by a processor via a communication interface, patient information associated with the identified patient including previous injection sites and previous injection results;
generating a target location on the patient for a new injection based on the patient information and prior to illuminating the patient with a light source of a vein detection device;
instructing a user of the vein detection device to illuminate the target location on the identified patient based on the patient information;
illuminating, by the light source of the vein detection device, the target location of the patient, the light source operating at a wavelength for penetrating the skin of the patient;
capturing, by a stereo camera of the vein detection device, an image in the illuminated target location, the stereo camera operating at the wavelength;
processing, by a processor, the captured image to detect a vein of the patient illuminated by the light source;
reconstructing, by the processor, a three-dimensional image of the detected vein based on the patient information and the processed captured image;
transmitting, by the processor, the three-dimensional image of the detected vein to a mobile device via a communication interface; and
following the new injection of the patient, transmitting injection results associated with the new injection to the medical server for updating the previous injection sites and previous injection results stored in the patient information.

11. The vein detection method according to claim 10, further comprising:
communicating, by the processor to the mobile device, via an interchangeable adaptor inserted into a port of the mobile device.

12. The vein detection method according to claim 10, further comprising:
instructing, by the processor via the communication interface, the server to store the reconstructed three-dimensional image of the detected vein.

13. The vein detection method according to claim 10, further comprising:
selecting, by the processor, an insertion point for a catheter and dimensions of the catheter based on physical characteristics of the detected vein in the three-dimensional image; and
transmitting, by the processor via the communication interface, the selected insertion point to the mobile device.

14. The vein detection method according to claim 10,
wherein the operating wavelength of the light source and the stereo camera is in the near infrared (NIR) spectrum.

15. The vein detection method according to claim 10, further comprising:
instructing, by the processor, the user of the vein detection device to adjust an orientation of the vein detection device while capturing the image.

16. The vein detection method according to claim 10, further comprising:

reconstructing, by the processor, the three dimensional image of the detected vein by determining a region of interest (ROI), extracting relevant vein features from the ROI, and performing 3D point cloud reconstruction of the relevant vein features.

17. The vein detection method according to claim 10, wherein the vein detection device comprises a housing, an interchangeable adaptor protruding from the housing for insertion into a port of the mobile device constituting a smartphone, and the cameras of the stereo camera and the light source being disposed on a same side surface of the housing.

18. The vein detection method according to claim 10, further comprising:

capturing, by the processor or the mobile device, an image of a code on a packaging of the catheter, on a medication label, on a patient's medical charts or on a patient's wrist band; and retrieving, by the mobile device using the code, information relating to at least one of the patient, the catheter, and the medication.

19. A method for displaying a suggested catheter insertion point, the method comprising the steps of:

generating a target location on a patient for a new injection based on patient information associated with the patient including previous injection sites and previous injection results, the generating step performed prior to illuminating the patient with a light source of a vein detection device, instructing a user of the vein detection device to illuminate the target location on the patient;

illuminating, by the light source of the vein detection device, the target location of the patient, the light source operating at a wavelength for penetrating the skin of the patient;

capturing, by a stereo camera of the vein detection device, an image in the illuminated target location, the stereo camera operating at the wavelength;

processing, by a processor, the captured image to detect a vein of the patient illuminated by the light source;

reconstructing, by the processor, a three-dimensional image of the detected vein based on medical records of the patient and the processed captured image;

displaying the three-dimensional image of the detected vein to a mobile device via a communication interface;

determining a suggested catheter insertion point based on the medical records of the patient and the processed captured image;

displaying the suggested catheter insertion point on the three-dimensional image for guiding the user in the insertion of a catheter; and following insertion of the catheter, transmitting insertion results associated with the injection to the medical server for updating the previous injection sites and previous injection results stored in the patient information.

20. The method for displaying a suggested catheter insertion point according to claim 19, further comprising:

displaying suggested catheter dimensions for guiding the user in the selection of the catheter.

21. The method for displaying a suggested catheter insertion point according to claim 19, further comprising:

displaying a suggested catheter insertion angle for guiding the user in the insertion of the catheter.

22. The method for displaying a suggested catheter insertion point according to claim 19, further comprising:

instructing the user to adjust an orientation of the vein detection device while capturing the image.

23. The method for displaying a suggested catheter insertion point according to claim 19, further comprising:

recording the suggested catheter insertion point in the medical records of the patient.

24. The method for displaying a suggested catheter insertion point according to claim 19, further comprising:

reconstructing, by the processor, the three dimensional image of the detected vein by determining a region of interest (ROI), extracting relevant vein features from the ROI and performing 3D point cloud reconstruction of the relevant vein features.

25. The method for displaying a suggested catheter insertion point according to claim 19, further comprising:

scanning an image of a barcode or QR code associated with the patient to identify the patient.

26. The method for displaying a suggested catheter insertion point according to claim 19, further comprising retrieving patient care information for the patient.

27. The method for displaying a suggested catheter insertion point according to claim 19, wherein the vein detection device comprises a housing, an interchangeable adaptor protruding from the housing for insertion into a port of the mobile device constituting a smartphone, and the cameras of the stereo camera and the light source being disposed on a same side surface of the housing.

28. The method for displaying a suggested catheter insertion point according to claim 19, further comprising:

capturing, by the processor or the mobile device, an image of a code on a packaging of the catheter, on a medication label, on a patient's medical charts or on a patient's wrist band; and retrieving, by the mobile device using the code, information relating to at least one of the patient, the catheter, and the medication.

29. The vein detection device according to claim 1, wherein patient information comprises age, weight, prior injection site results, prior injection site recommendations, or a combination thereof.

30. The vein detection device according to claim 1, further comprising an indicator for marking a location of an insertion point for a catheter.

31. The vein detection device according to claim 30, wherein the indicator comprises an arrow or an opening.

32. The vein detection device according to claim 30, wherein the processor is further configured to select the insertion point for the catheter and dimensions of the catheter based on physical characteristics of the detected vein in the three-dimensional image, and transmit the selected insertion point to the mobile device.

33. The vein detection device according to claim 32, wherein the processor is configured to transmit instructions to the mobile device, the instructions comprising aligning the indicator with the selected insertion point.

34. The vein detection device according to claim 33, wherein aligning the indicator with the selected insertion point permits the caregiver to insert the catheter at the marked insertion point while the vein detection device is positioned on the patient's skin.

* * * * *